US009868754B2

(12) United States Patent
Choe et al.

(10) Patent No.: US 9,868,754 B2
(45) Date of Patent: Jan. 16, 2018

(54) UTILITY OF NEMATODE SMALL MOLECULES

(75) Inventors: Andrea Choe, Pasadena, CA (US); Paul W. Sternberg, San Marino, CA (US); Frank C. Schroeder, Ithaca, NY (US); Stephan H. Von Reuss, Jena (DE)

(73) Assignees: California Institute of Technology, Pasadena, CA (US); Boyce Thompson Institute for Plant Research, Ithaca, NY (US)

( * ) Notice: Subject to any disclaimer, the term of this patent is extended or adjusted under 35 U.S.C. 154(b) by 158 days.

(21) Appl. No.: 14/237,795

(22) PCT Filed: Aug. 8, 2012

(86) PCT No.: PCT/US2012/050031
§ 371 (c)(1),
(2), (4) Date: May 30, 2014

(87) PCT Pub. No.: WO2013/022996
PCT Pub. Date: Feb. 14, 2013

(65) Prior Publication Data
US 2015/0018291 A1 Jan. 15, 2015

Related U.S. Application Data

(60) Provisional application No. 61/620,348, filed on Apr. 4, 2012, provisional application No. 61/620,331, filed on Apr. 4, 2012, provisional application No. 61/620,343, filed on Apr. 4, 2012, provisional application No. 61/521,295, filed on Aug. 8, 2011.

(51) Int. Cl.
A61K 31/7028 (2006.01)
C07H 15/04 (2006.01)
A01N 37/36 (2006.01)
A01N 63/02 (2006.01)
A61K 31/454 (2006.01)
C07H 15/08 (2006.01)
C07H 15/10 (2006.01)
C07H 15/18 (2006.01)
C07H 15/26 (2006.01)
A01N 43/16 (2006.01)
A01N 43/38 (2006.01)
C07D 309/10 (2006.01)

(52) U.S. Cl.
CPC ............ C07H 15/04 (2013.01); A01N 37/36 (2013.01); A01N 43/16 (2013.01); A01N 43/38 (2013.01); A01N 63/02 (2013.01); A61K 31/454 (2013.01); A61K 31/7028 (2013.01); C07H 15/08 (2013.01); C07H 15/10 (2013.01); C07H 15/18 (2013.01); C07H 15/26 (2013.01); C07D 309/10 (2013.01)

(58) Field of Classification Search
None
See application file for complete search history.

(56) References Cited

U.S. PATENT DOCUMENTS

| 5,945,445 | A | 8/1999 | Barringer et al. |
| 6,444,686 | B1 * | 9/2002 | Ko .................... C07D 207/06 514/278 |
| 8,318,146 | B1 | 11/2012 | Teal et al. |
| 2005/0075389 | A1 | 4/2005 | Paik et al. |
| 2008/0188646 | A1 | 8/2008 | Jung et al. |
| 2010/0048497 | A1 | 2/2010 | Andersch et al. |
| 2010/0056469 | A1 | 3/2010 | Langewald et al. |
| 2014/0303102 | A1 | 10/2014 | Choe et al. |
| 2014/0303360 | A1 | 10/2014 | Schroeder et al. |
| 2014/0364386 | A1 | 12/2014 | Choe et al. |

FOREIGN PATENT DOCUMENTS

| DE | 10163602 | * | 7/2003 |
| KR | 10-2009-0088496 | | 8/2009 |
| WO | WO-96/19920 | | 7/1996 |
| WO | WO-2004/043944 A1 | | 5/2004 |
| WO | WO-2005/075491 A1 | | 8/2005 |
| WO | WO-2005/110040 A2 | | 11/2005 |
| WO | WO-2009/102736 | | 8/2009 |
| WO | WO-2013/022985 A2 | | 2/2013 |
| WO | WO-2013/022997 A2 | | 2/2013 |
| WO | WO-2013/023000 A2 | | 2/2013 |

OTHER PUBLICATIONS

Butcher, Rebecca A., et al. "An Indole-Containing Dauer Pheromone Component with Unusual Dauer Inhibitory Activity at Higher Concentrations," Organic Letters 11(14): 3100-3103 (May 9, 2009).
Butcher, R.A., et al. "Biosynthesis of the Caenorhabditis elegans dauer pheromone," Proceedings of the National Academy of Sciences, 106(6): 1875-1879 (Feb. 10, 2009).
Butcher, R. A. "Small-molecule pheromones that control dauer development in Caenorhabditis elegans," J. Nat. Chem. Biol. 3(7): 420-422 (2007).
Choe, Andrea, "Pheromones in Free-Living and Parasitic Nematodes," Thesis for California Institute of Technology, (Jun. 17, 2011) (Made publically available Dec. 2, 2013).
Chuman, T., et al. "Identification and Characterization of Nematode Pheromones," National High Magnetic Field Laboratory (Jan. 1, 2009).
European C. elegans Neurobiology Meeting; Oct. 9, 2010. (http://www.worms.gr/ewnm2010/files/abstracts.pdf).

(Continued)

Primary Examiner — Traviss C McIntosh, III
(74) Attorney, Agent, or Firm — Foley Hoag LLP

(57) ABSTRACT

The present invention relates to methods of treating immune disorders and/or inflammation using certain modulator compounds. In one embodiment, the present invention provides a method of treating an immune and inflammatory disorders disorder by administering a composition comprising a therapeutically effective dosage of an ascaroside compound, or a mixture of ascaroside compounds, or a mixture containing at least one ascaroside.

6 Claims, 16 Drawing Sheets

(56) References Cited

OTHER PUBLICATIONS

Kaplan, F. et al. "Ascaroside Expression in *Caenorhabditis elegans* Is Strongly Dependent on Diet and Developmental Stage," PLOSOne, 6(3): e17804 (Mar. 2011).
Martin, R., et al. "Improved Synthesis of an Ascaroside Pheromone Controlling Dauer Larva Development in Caenorhabditis Elegans," Synthesis, 20: 3488 (2009).
Pungaliya, C., et al. "A shortcut to identifying small molecule signals that regulate behavior and development in Caenorhabditis elegans," Proceedings of the National Academy of Sciences, 106(19): 7708-7713 (May 12, 2009).
Von Reuss, Stephan H., et al. "Comparative Metabolomics Reveals Biogenesis of Ascarosides, a Modular Library of Small-Molecule Signals in *C. elegans*," Journal of the American Chemical Society, 134(3): 1817-1824; (Jan. 25, 2012).
European Extended Search Report for EP Patent Application: 12822698.2 dated Mar. 4, 2015.
International Search Report dated Jul. 25, 2013 from PCT/US2012/050016.
International Search Report dated May 2, 2013 from PCT/US2012/050032.
Choe et al., "Ascaroside Signaling is Widely Conserved Among Nematodes," Curr Biol., 22(9):772-780 (2012).
Gallo et al., "Effects of a Caenorhabditis elegans dauer pheromone ascaroside on physiology and signal transduction pathways," J. Chem. Ecol., 35(2):272-279 (2009).
Jeong et al., "Chemical structure and biological activity of the Caenorhabditis elegans dauer-inducing pheromone," Nature, 433(7025):541-545 (2005).
Noh et al., "Quantitative determination of daumone in rat plasma by liquid chromatography-mass spectrometry," J. Pharm. Biomed. Anal., 56(1):114-117 (2011).
Ben-Yakir, D. et al., "Evaluation of entomopathogenic nematodes for biocontrol of the European Corn Borer, *Ostrinia nubilalis*, on sweet corn in Israel," Phytoparasitica, 26(2):101-8 (1998).
Bose et al., "Complex small-molecule architectures regulate phenotypic plasticity in a nematode," Angew Chem Int Ed, 51:12438-43 (2012).
Cheng et al., "Insertional mutagenesis of a fungal biocontrol agent led to discovery of a rare cellobiose lipid with antifungal activity," Appl Environ Microb, 69(5):2595-602 (2003).
Lacey, L.A. et al., "Insect pathogens as biological control agents: Do they have a future?" Biol Control, 21:230-48 (2001).
Riga, E. et al., "In vitro effect of marigold seed exudates on plant parasitic nematodes," Phytoprotection, 86:31-5 (2004).
Srinivasan et al., "A blend of small molecules regulates both mating and development in *Caenorhabditis elegans*," Nature, 454:1115-9 (2008).

\* cited by examiner

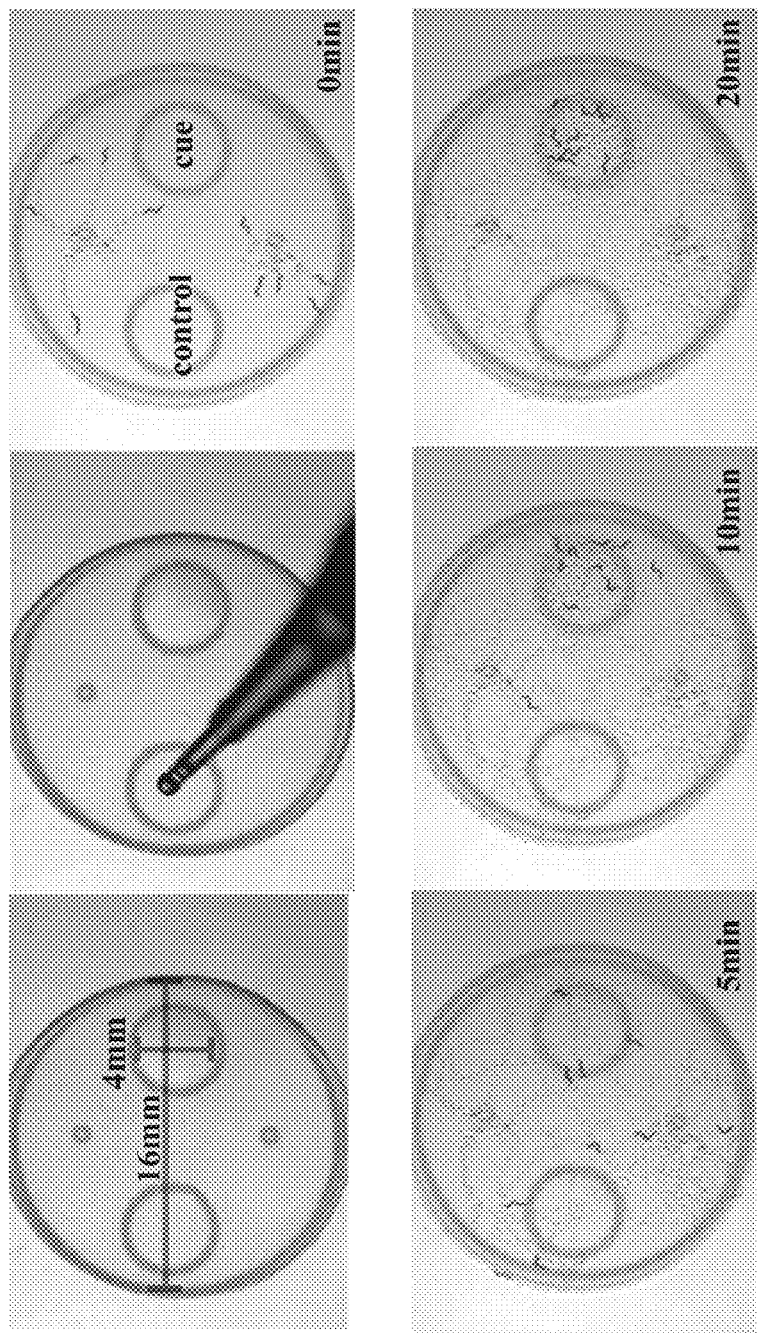

Figure 2
A     Purification of *Panagrellus redivivus* male sex pheromone
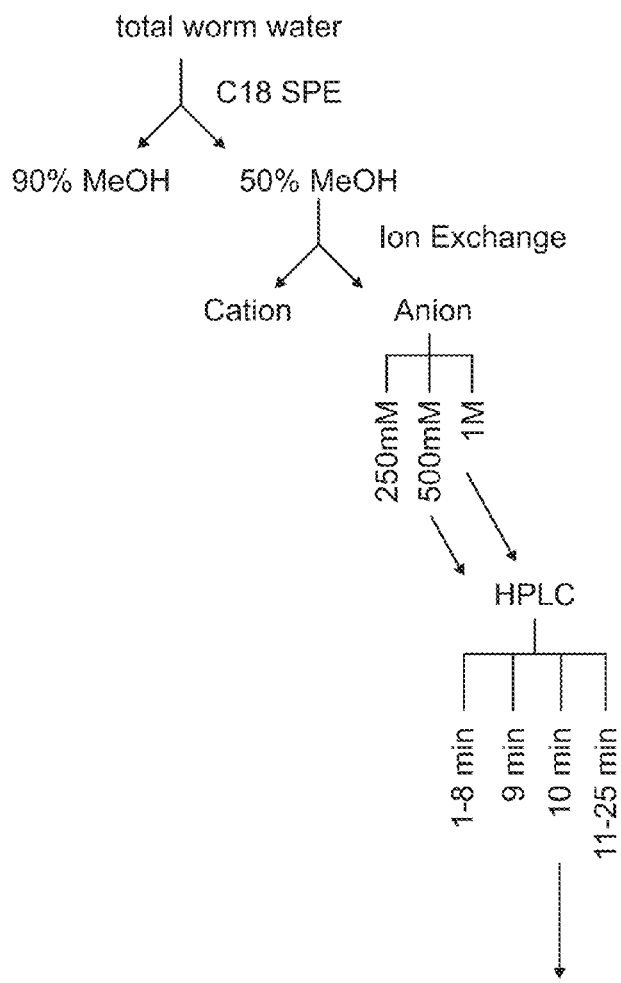
LCMS and NMR leads to identication of ascr#1.
Synthesize and test ascr#1 on both males & females
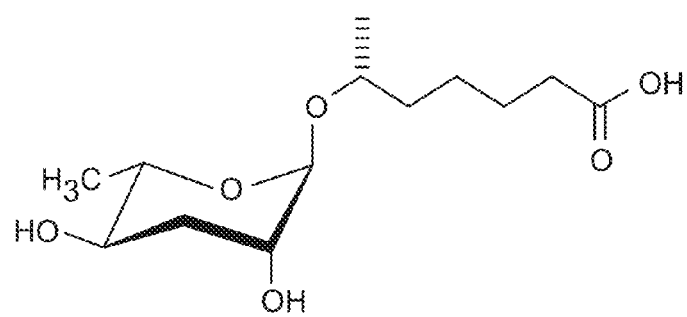

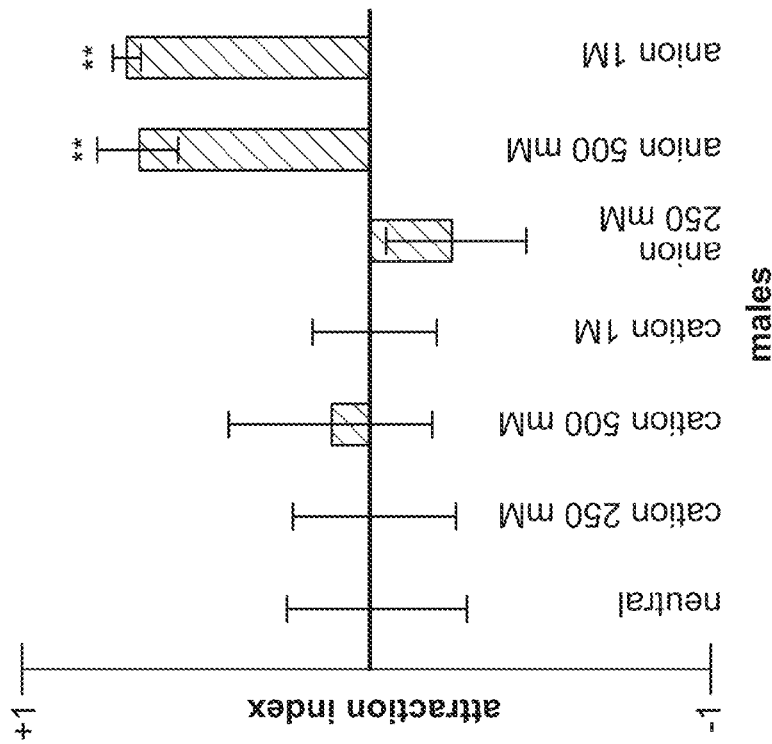
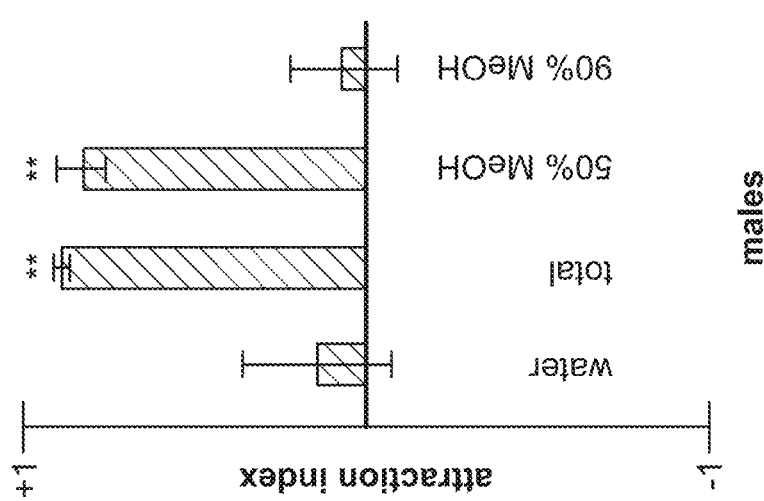
Figure 2 (cont.)

Figure 2 (cont.)
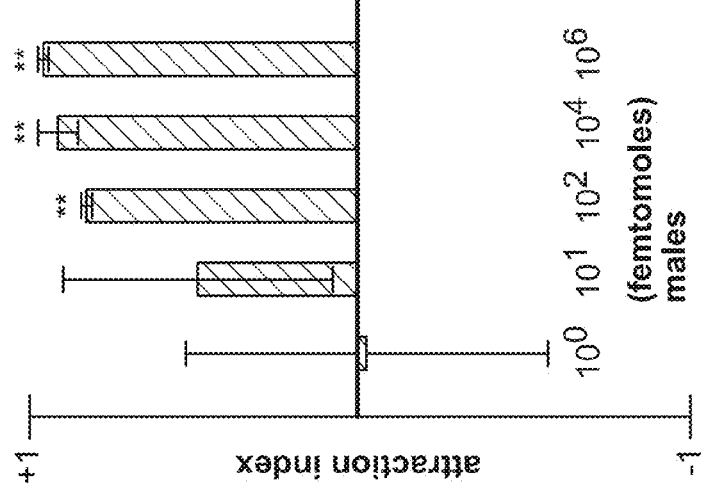
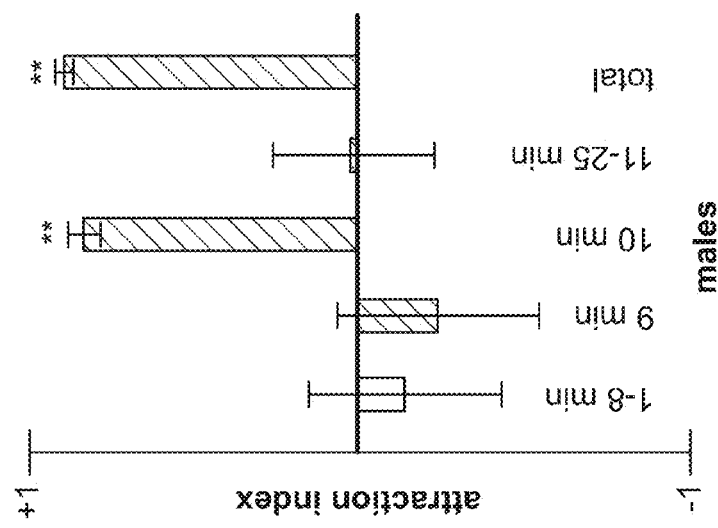

Figure 3 (cont.)
D
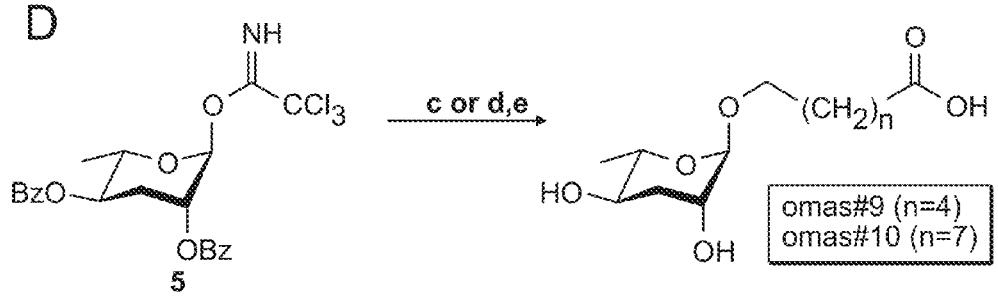
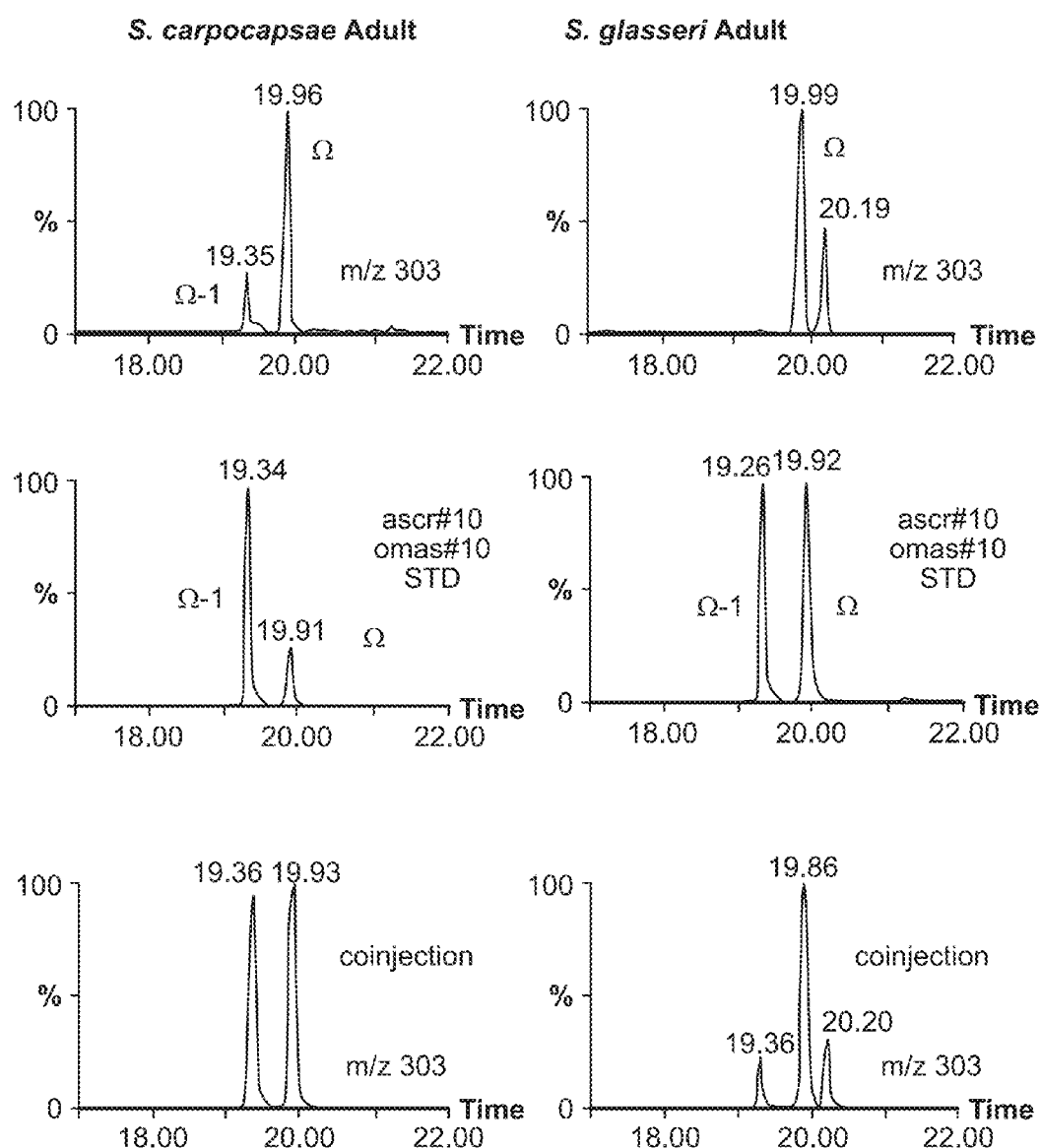

Figure 7
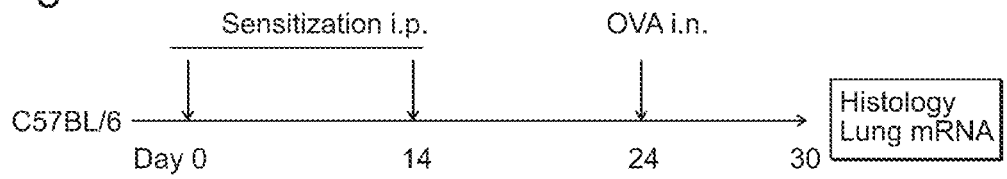
A  HE staining
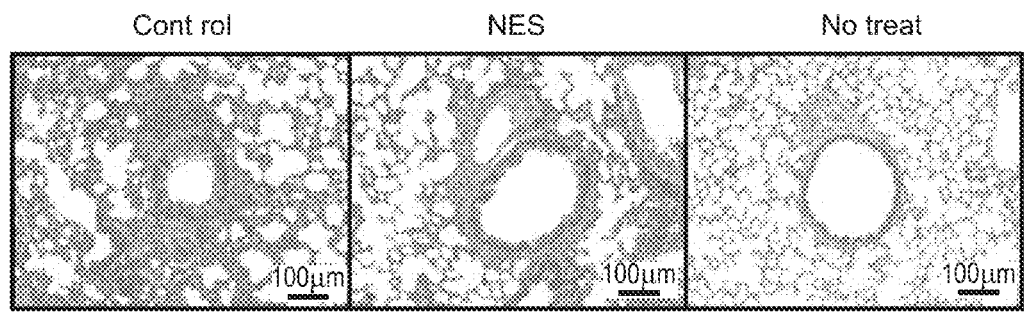
B  PAS staining
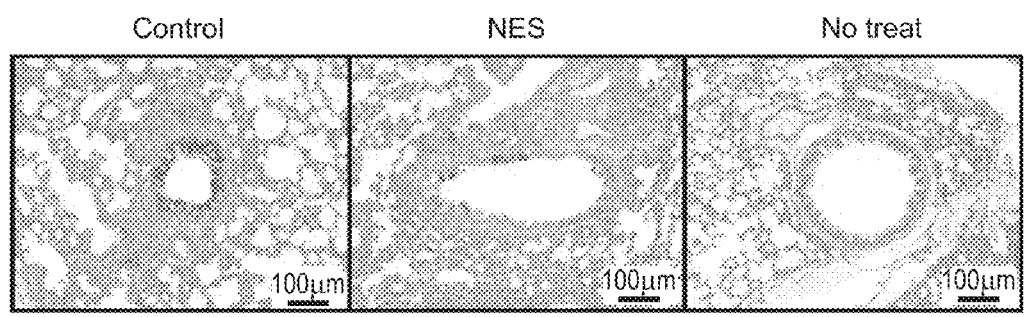
C  Lung mRNA
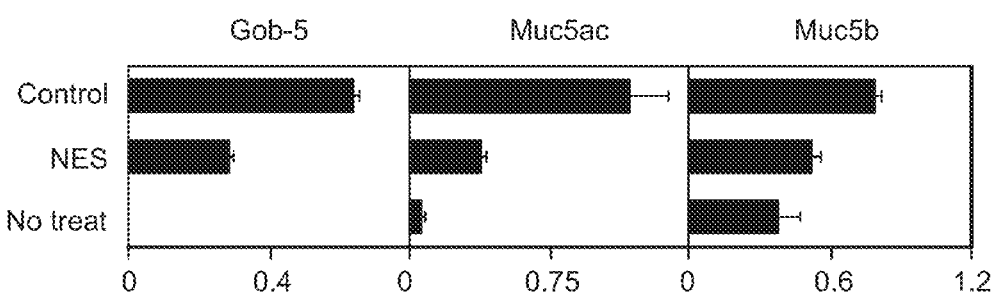

UTILITY OF NEMATODE SMALL MOLECULES

This application is a §371 national-stage application based on Patent Cooperation Treaty Application serial number PCT/US2012/050031, filed Aug. 8, 2012, which claims the benefit of priority to U.S. Provisional Patent Application Ser. No. 61/521,295, filed Aug. 8, 2011, and U.S. Provisional Patent Application Ser. No. 61/620,343, filed on Apr. 4, 2012, and U.S. Provisional Application Ser. No. 61/620,331, filed on Apr. 4, 2012, and U.S. Provisional Patent Application Ser. No. 61/620,348, each of which is hereby incorporated by reference in its entirety.

GOVERNMENT RIGHTS

This invention was made with United States Government support under NIH Agreement No. GM085285. The Government has certain rights in the invention.

FIELD OF THE INVENTION

The invention relates to the field of biotechnology, specifically to immunomodulation and nematodes.

BACKGROUND OF THE INVENTION

All publications herein are incorporated by reference to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

Nematodes are the most abundant animals in the world, found to inhabit sulfurous sediment, deep-sea trenches, human lymph nodes, pig intestines, plant roots, whale placenta, arctic ice, and many other ecosystems, making them one of the most successful groups of animals on earth. Many nematode species are known to parasitize humans; a relationship that is thought to have existed for thousands of years.

The rise of immune disorders in the industrialized world has been concomitant with the decline of endemic parasitisim, lending way to the etiologic theory that humans are creating an inappropriate immune response that had previously been focused on overcoming the suppressive mechanisms of parasites. Nematodes have been in use to treat some immune disorders. There is a need in the art to develop novel compounds and methods of treating, alleviating, and/or preventing an adverse immune response and/or disorder in the place of live organisms.

SUMMARY OF THE INVENTION

Small molecules produced specifically by nematodes can mimic the presence of nematodes and thus be used to promote health. Various embodiments include a method of alleviating, treating, or preventing a disorder in a subject, comprising the provision of a composition comprising a compound of the formula:

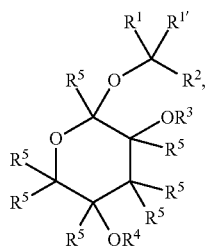
(Formula I)

or a pharmaceutical equivalent, derivative, analog and/or salt thereof, and administering a therapeutically effective dosage of the composition to the subject. In another embodiment, the disorder is an inflammatory and/or immune disorder. In another embodiment, $R^1$ is H, —$C(R)_3$, —OR, —$N(R)_2$, halogen, an alkyl, a haloalkyl, an alkenyl, or a haloalkenyl. In another embodiment, $R^{1'}$ is absent, H, —$C(R)_3$, —OR, —$N(R)_2$, halogen, an alkyl, a haloalkyl, an alkenyl, or a haloalkenyl. In another embodiment, $R^2$ is a moiety of the formula:

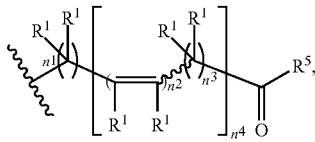
(Formula II)

or a pharmaceutical equivalent, derivative, analog and/or salt thereof. In another embodiment, $R^3$ is H, —$CR^6R^7R^8$, —$C(O)R^8$, an alkyl, a haloalkyl, an alkenyl, a haloalkenyl, an aryl, a heteroaryl, a heterocyclyl, a cycloalkyl, a cycloalkenyl, an acyl, an amino acid, a nucleoside, a monosaccharide having 5 or 6 carbon atoms, or a bond connecting to $R^5$ of another unit of Formula I. In another embodiment, $R^4$ is H, —$CR^6R^7R^8$, —$C(O)R^8$, an alkyl, a haloalkyl, an alkenyl, a haloalkenyl, an aryl, a heteroaryl, a heterocyclyl, a cycloalkyl, a cycloalkenyl, an acyl, an amino acid, a nucleoside, a monosaccharide having 5 or 6 carbon atoms, or a bond connecting to $R^5$ of another unit of Formula I. In another embodiment, $R^5$ is H, —OH, —$OR^6$, —$OCR^6R^7R^8$, —$CR^6R^7R^8$, —$NH_2$, —$NHR^6$, —$NR^6R^7$, halogen, an alkyl, a haloalkyl, an alkenyl, a haloalkenyl, an aryl, a heteroaryl, an arylalkyl, a heterocyclyl, a cycloalkyl, a cycloalkenyl, an acyl, an amino acid, a nucleoside, a monosaccharide having 5 or 6 carbon atoms, or a bond connecting to $R^3$ or $R^4$ of another unit of Formula I. In another embodiment, the disorder is acne vulgaris, asthma, autoimmune diseases, celiac disease, chronic prostatitis, glomerulonephritis, Hypersensitivities, Inflammatory bowel diseases, pelvic inflammatory disease, reperfusion injury, rheumatoid arthritis, sarcoidosis, transplant rejection, vasculitis, Interstitial cystitis, lupus, scleroderma, certain types of hemolytic anemia, type one diabetes, graves disease, multiple sclerosis, Goodpasture's syndrome, pernicious anemia, some types of myopathy, seasonal allergy, mastocytosis, perennial allergy, anaphylaxis, food allergy, allergic rhinitis, atopic dermatitis, and/or autism. In another embodiment, the disorder is asthma. In another embodiment, the subject is a human. In another embodiment, the subject is selected from the group consisting of primates, humans, equines, horses, cattle, cows, swine, sheep, rodents, rats, pets, cats, dogs, and guinea pigs. In another embodiment, the composition comprises one or more compounds selected from the group consisting of ascr#1, ascr#3, ascr#7, ascr#8, ascr#9, and ascr#10.

Other embodiments include a method of reducing inflammation in a subject, comprising providing a composition comprising a compound of the formula:

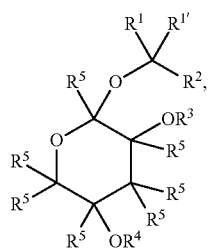

(Formula I)

or a pharmaceutical equivalent, derivative, analog and/or salt thereof, and administering a therapeutically effective dosage of the composition to the subject. In another embodiment, $R^1$ is H, —C(R)$_3$, —OR, —N(R)$_2$, halogen, an alkyl, a haloalkyl, an alkenyl, or a haloalkenyl. In another embodiment, $R^{1'}$ is absent, H, —C(R)$_3$, —OR, —N(R)$_2$, halogen, an alkyl, a haloalkyl, an alkenyl, or a haloalkenyl. In another embodiment, $R^2$ is a moiety of the formula:

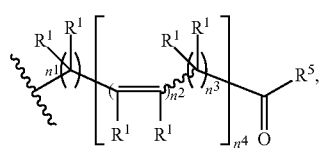

(Formula II)

or a pharmaceutical equivalent, derivative, analog and/or salt thereof. In another embodiment, $R^3$ is H, —CR$^6$R$^7$R$^8$, —C(O)R$^8$, an alkyl, a haloalkyl, an alkenyl, a haloalkenyl, an aryl, a heteroaryl, a heterocyclyl, a cycloalkyl, a cycloalkenyl, an acyl, an amino acid, a nucleoside, a monosaccharide having 5 or 6 carbon atoms, or a bond connecting to $R^5$ of another unit of Formula I. In another embodiment, $R^4$ is H, —CR$^6$R$^7$R$^8$, —C(O)R$^8$, an alkyl, a haloalkyl, an alkenyl, a haloalkenyl, an aryl, a heteroaryl, a heterocyclyl, a cycloalkyl, a cycloalkenyl, an acyl, an amino acid, a nucleoside, a monosaccharide having 5 or 6 carbon atoms, or a bond connecting to $R^5$ of another unit of Formula I. In another embodiment, $R^5$ is H, —OH, —OR$^6$, —OCR$^6$R$^7$R$^8$, —CR$^6$R$^7$R$^8$, —NH$_2$, —NHR$^6$, —NR$^6$R$^7$, halogen, an alkyl, a haloalkyl, an alkenyl, a haloalkenyl, an aryl, a heteroaryl, an arylalkyl, a heterocyclyl, a cycloalkyl, a cycloalkenyl, an acyl, an amino acid, a nucleoside, a monosaccharide having 5 or 6 carbon atoms, or a bond connecting to $R^3$ or $R^4$ of another unit of Formula I. In another embodiment, further comprising a reduction in eosinophils in the subject. In another embodiment, further comprising a reduction in mucus production in the subject. In another embodiment, the subject is a human. In another embodiment, the subject is selected from the group consisting of primates, humans, equines, horses, cattle, cows, swine, sheep, rodents, rats, pets, dogs, and guinea pigs. In another embodiment, the composition comprises one or more compounds selected from the group consisting of ascr#1, ascr#3, ascr#7, ascr#8, ascr#9, and ascr#10. In another embodiment, the composition comprises an scaroside naturally produced by a nematode. In another embodiment, the composition comprises an ascaroside naturally produced from a *Nippostrongylus brasiliensis*. In another embodiment, the inflammation is associated with *acne vulgaris*, asthma, autoimmune diseases, celiac disease, chronic prostatitis, glomerulonephritis, Hypersensitivities, Inflammatory bowel diseases, pelvic inflammatory disease, reperfusion injury, rheumatoid arthritis, sarcoidosis, transplant rejection, vasculitis, Interstitial cystitis, lupus, *scleroderma*, certain types of hemolytic anemia, type one diabetes, graves disease, multiple sclerosis, Goodpasture's syndrome, pernicious anemia, some types of myopathy, seasonal allergy, mastocytosis, perennial allergy, anaphylaxis, food allergy, allergic rhinitis, atopic dermatitis, and/or autism.

Other features and advantages of the invention will become apparent from the following detailed description, taken in conjunction with the accompanying drawings, which illustrate, by way of example, various embodiments of the invention.

BRIEF DESCRIPTION OF THE DRAWINGS

Exemplary embodiments are illustrated in referenced figures. It is intended that the embodiments and figures disclosed herein are to be considered illustrative rather than restrictive.

FIG. 1(a) depicts a chemoattraction assay. A transparent template is attached below a 5-cm plate with a 16-mm bacterial lawn to delineate two scoring regions into which 0.64, of the experimental sample and control sample are placed. Ten *P. redivivus* males are placed at points equidistant from the two scoring regions and the plate is recorded for 20 minutes (at a rate of 1 frame per second). FIG. 1(b) depicts attraction is measured using software that computes the ratio of worm-pixels to total pixels for each scoring region (left panels). The output is a plot of worm occupancy ratio vs. time for both scoring regions (right panel). The shown graph indicates strong attraction of *P. redivivus* males to the experimental sample.

FIG. 2 depicts, in accordance with an embodiment herein, purification of the female sex pheromone in *Panagrellus redivivus*. FIG. 2(a) depicts *Panagrellus redivivus* were grown in mixed-gender liquid cultures and the total supernatant was fractionated using C18 solid phase extraction, ion exchange, and high performance liquid chromatography. Male attraction was measured via the Attraction Bioassay (see FIG. 1). FIG. 2(b) depicts the total worm water was divided using 50% MeOH and 90% MeOH extractions via C18 SPE, with significant male attraction to both the combined fractions (total) and 50% MeOH fraction. FIG. 2(c) depicts the 50% MeOH fraction was subdivided using ion exchange, with no male attraction to the cation fractions and significant attraction to both the 500 mM and 1M anion fractions. FIG. 2(d) depicts the 500 mM and 1M anion fractions were further subdivided using HPLC. The compound eluted at 10 minutes produced full male attraction, which was then identified as ascr#1 using liquid chromatography mass spectrometry (LCMS) and nuclear magnetic resonance (NMR). FIG. 2(e) depicts ascr#1 was then synthesized and tested at different doses, demonstrating that males were attracted to ascr#1 at concentrations between 102 fmol and 106 fmol whereas females were not attracted to ascr#1 between 100 and 106 fmol. Error bars, S.D. P values were determined using Student's t-test.** P<0.01.

FIG. 7 depicts, in accordance with an embodiment herein, sensitization with OVA+Control/Alum (N=3) and sensitization with OVA+NES/Alum (N=3), in *Nippostrongylus brasiliensis*. The experimental model is ovalbumin inducation of asthma. FIG. 7 further depicts lung histology which shows marked reduction in the inflammation when asthmatic mice were given total* hookworm supernatant, as measured by decreased cellular infiltration and decreased mucus hyper-production. Quantitative mRNA analysis demonstrates diminished expression of genes associated with mucus production. * Total hookworm water=worms cultured in media, worms filtered out. No worm, living or dead, is introduced into the asthma model. Furthermore, proteins were eliminated by denaturing at 100 C for 25 minutes, and filtering through a 10 kDa filter. FIG. 7 depicts the histology of mice treated with NES. FIG. 7A shows HE staining of lung sections. The intense infiltration of inflammatory cells, predominantly eosinophils, into the lungs was observed near the bronchioles and vessels of mice sensitized with Control+OVA. When mice were sensitized with NES together with OVA, the cellular infiltration into the lungs was dramatically reduced. FIGS. 7B and 7C shows PAS (periodic acid-Schiff) staining and the measurement of mRNA expression of Gob5, Muc5a/c and Muc5b in the lung indicated a decrease in mucus hyperproduction in mice sensitized with NES together with OVA.

DETAILED DESCRIPTION

Figure 1:
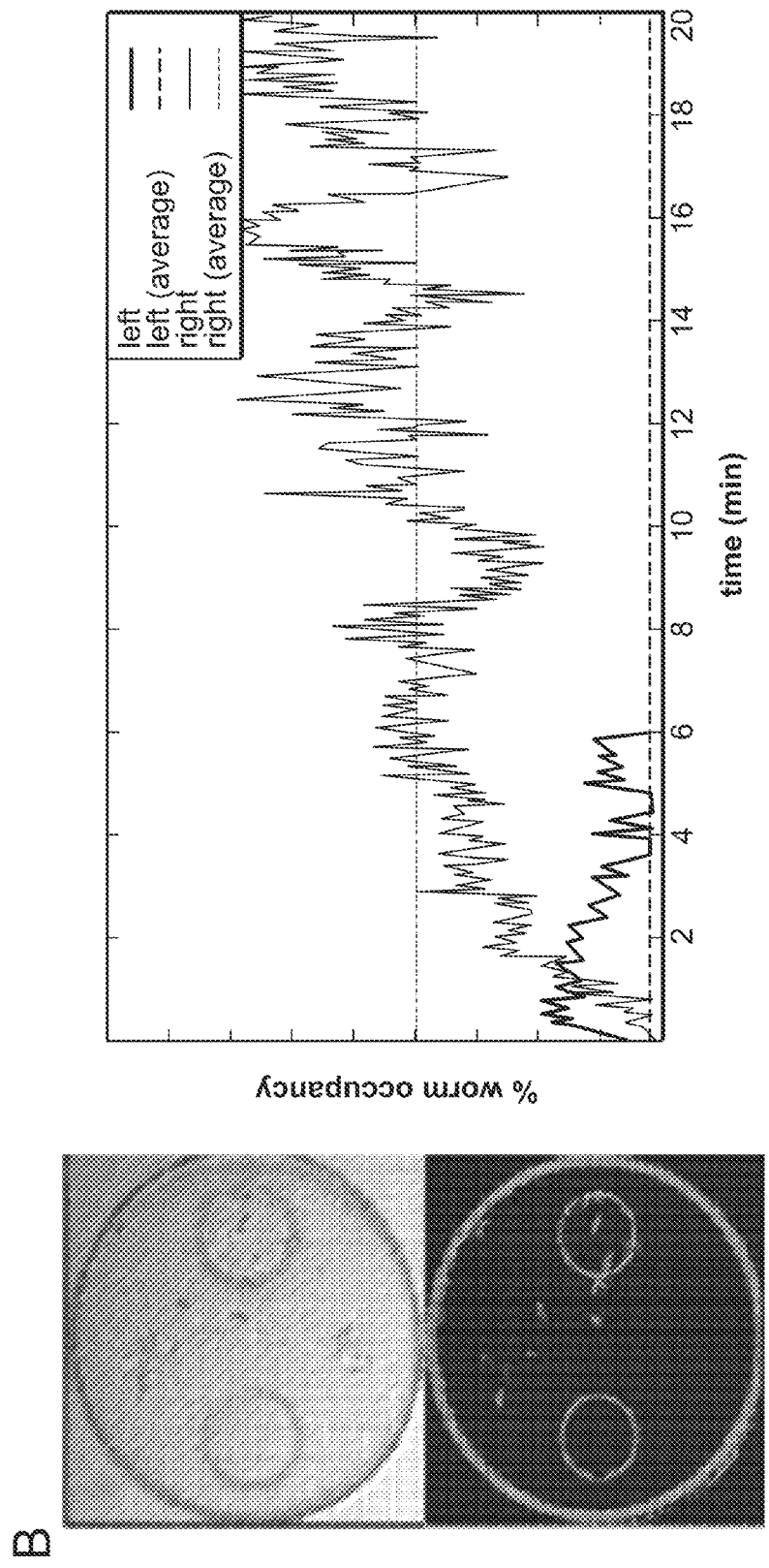
FIG. 1 depicts, in accordance with an embodiment herein, chemoattraction assay to reveal a gender specific mate finding cue in *Panagrellus redivivus*.
Figure 3:
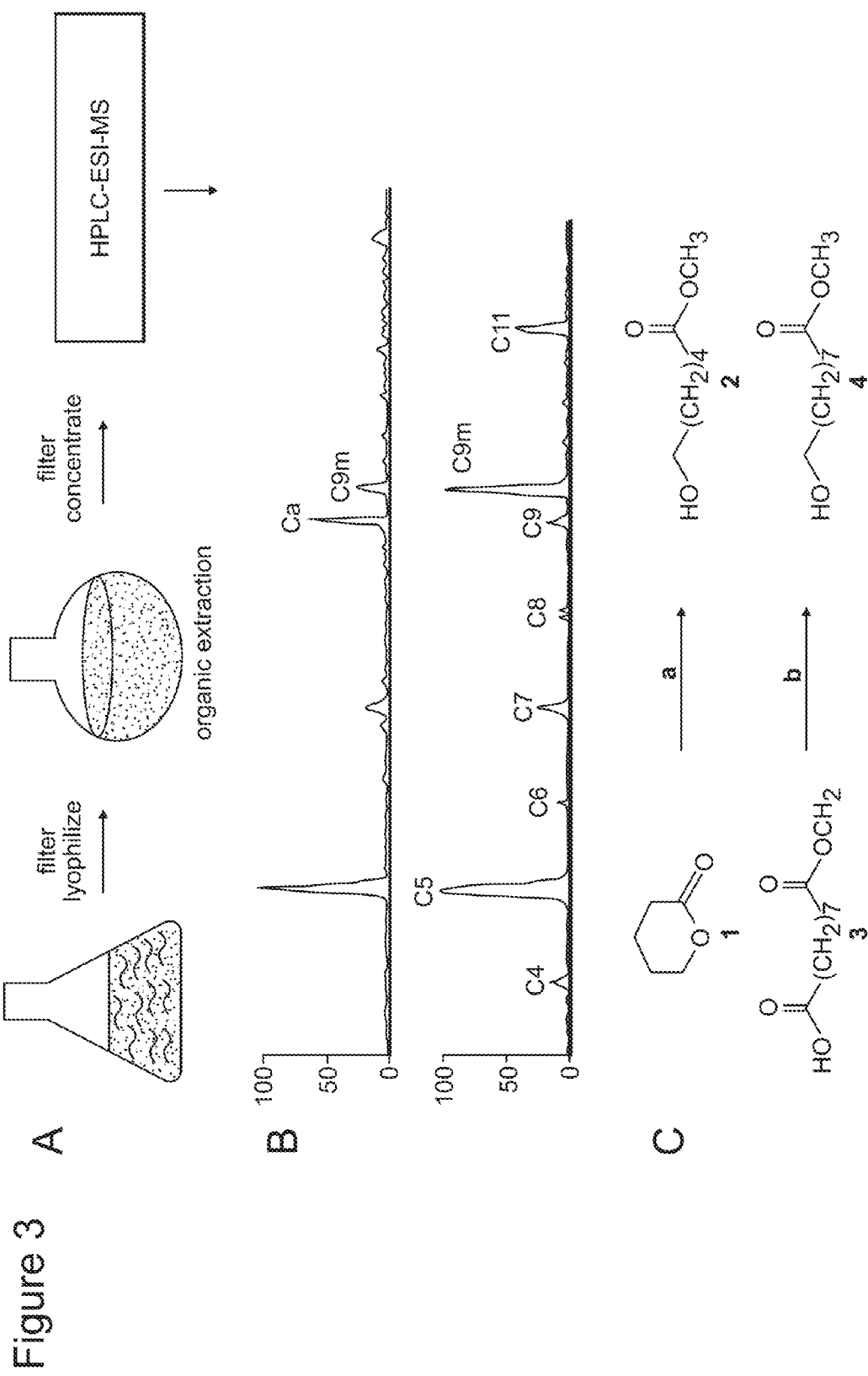
FIG. 3 depicts methods for HPLC-ESI-MS.

All references cited herein are incorporated by reference in their entirety as though fully set forth. Unless defined otherwise, technical and scientific terms used herein have the same meaning as commonly understood by one of ordinary skill in the art to which this invention belongs. Singleton et al., Dictionary of Microbiology and Molecular Biology 3rd ed., J. Wiley & Sons (New York, N.Y. 2001); March, Advanced Organic Chemistry Reactions, Mechanisms and Structure 5th ed., J. Wiley & Sons (New York, N.Y. 2001); and Sambrook and Russel, Molecular Cloning: A Laboratory Manual 3rd ed., Cold Spring Harbor Laboratory Press (Cold Spring Harbor, N.Y. 2001), provide one skilled in the art with a general guide to many of the terms used in the present application.

One skilled in the art will recognize many methods and materials similar or equivalent to those described herein, which could be used in the practice of the present invention. Indeed, the present invention is in no way limited to the methods and materials described. For purposes of the present invention, the following terms are defined below.

As used herein, the following terms, unless otherwise indicated, shall be understood to have the following meanings. If not defined otherwise herein, all technical and scientific terms used herein have the same meaning as is commonly understood by one of ordinary skill in the art to which this invention belongs. In the event that there is a plurality of definitions for a term herein, those in this section prevail unless stated otherwise.

The term "alkyl" refers to an aliphatic hydrocarbon group which may be a linear, branched, or cyclic hydrocarbon structure or combination thereof. Representative alkyl groups are those having 24 or fewer carbon atoms, for instance, methyl, ethyl, n-propyl, i-propyl, n-butyl, s-butyl, t-butyl, n-pentyl, i-pentyl, n-hexyl, and the like. Lower alkyl refers to alkyl groups having about 1 to about 6 carbon atoms in the chain. Branched alkyl means that one or more lower alkyl groups such as methyl, ethyl, or propyl are attached to a linear alkyl chain.

The statement that alkyl is intended to include linear, branched, or cyclic hydrocarbon structures and combinations thereof means that an "alkyl" group also includes the following combination of linear and cyclic structural elements

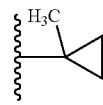

(and similar combinations).

"Alkenyl" means an alkyl, as defined above, containing at least one double bond between adjacent carbon atoms. Alkenyls include both cis and trans isomers. Branched alkenyl means that one or more lower alkyl groups such as methyl, ethyl, or propyl are attached to a linear alkenyl chain. Representative straight chain and branched alkenyls are those having about 2 to about 6 carbon atoms in the chain, for instance, ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like.

The term "halogen" refers to fluoro, chloro, bromo, and iodo.

The term "haloalkyl" refers to a branched or straight-chain alkyl as described above, substituted with one or more halogens.

The term "haloalkenyl" refers to a branched or straight-chain alkenyl as described above, substituted with one or more halogens.

The term "aryl" means an aromatic monocyclic or multi-cyclic (polycyclic) ring system of 6 to about 19 carbon atoms, for instance, about 6 to about 10 carbon atoms, and includes arylalkyl groups. Representative aryl groups include, but are not limited to, groups such as phenyl, naphthyl, azulenyl, phenanthrenyl, anthracenyl, fluorenyl, pyrenyl, triphenylenyl, chrysenyl, and naphthacenyl.

The term "arylalkyl" means an alkyl residue attached to an aryl ring. Examples are benzyl, phenethyl, and the like.

The term "heteroaryl" means an aromatic monocyclic or multi-cyclic ring system of about 5 to about 19 ring atoms, for instance, about 5 to about 10 ring atoms, in which one or more of the atoms in the ring system is/are element(s) other than carbon, for example, nitrogen, oxygen, and/or sulfur. As is well known to those skilled in the art, heteroaryl rings have less aromatic character than their all-carbon counterparts. Thus, for the purposes of the invention, a "heteroaryl" group need only have some degree of aromatic character. For instance, in the case of multi-cyclic ring systems, only one of the rings needs to be aromatic for the ring system to be defined as "heteroaryl". Exemplary heteroaryls contain about 5 to 6 ring atoms. The prefix aza, oxa, thia, or thio before heteroaryl means that at least a nitrogen, oxygen, or sulfur atom, respectively, is present as a ring atom. A nitrogen, carbon, or sulfur atom in the heteroaryl ring may be optionally oxidized; the nitrogen may optionally be quaternized. Representative heteroaryls include, but are not limited to, purinyl, pyridyl, 2-oxo-pyridinyl, pyrimidinyl, pyridazinyl, pyrazinyl, triazinyl, furanyl, pyrrolyl, thiophenyl, pyrazolyl, imidazolyl, oxazolyl, isoxazolyl, thiazolyl, isothiazolyl, triazolyl, oxadiazolyl, thiadiazolyl, tetrazolyl, indolyl, isoindolyl, benzofuranyl, benzothiophenyl, indolinyl, 2-oxoindolinyl, dihydrobenzofuranyl, dihydrobenzothiophenyl, indazolyl, benzimidazolyl, benzooxazolyl, benzothiazolyl, benzoisoxazolyl, benzoisothiazolyl, benzotriazolyl, quinolinyl, isoquinolinyl, quinazolinyl, cinnolinyl, pthalazinyl, quinoxalinyl, and the like.

The terms "cycloalkyl" and "cycloalkenyl" refer to a non-aromatic, saturated (cycloalkyl) or unsaturated (cycloalkenyl), mono- or multi-cyclic ring system of about 3 to about 8 carbon atoms, for instance, about 5 to about 7 carbon atoms. Exemplary cycloalkyl and cycloalkenyl groups include, without limitation, cyclopropyl, cyclobutyl, cyclopentyl, cyclohexyl, cycloheptyl, norbornyl, cyclopropenyl, cyclobutenyl, cyclopentenyl, cyclohexenyl, cyclophenyl, anti-bicyclopropane, syn-tricyclopropane, and the like.

As used herein, "heterocycle" or "heterocyclyl" refers to a stable 3- to 18-membered ring (radical) which is saturated, unsaturated, or aromatic, and which consists of carbon atoms and from one to five heteroatoms selected from the group consisting of nitrogen, oxygen and sulfur. For purposes of this invention, the heterocycle may be a monocyclic, bicyclic, or a polycyclic ring system, which may include fused, bridged, or spiro ring systems, including bicyclic rings in which any of the above heterocycles are fused to a benzene ring. The nitrogen, carbon, or sulfur atoms in the heterocycle may be optionally oxidized; the nitrogen atom may be optionally quaternized; and the ring may be partially or fully saturated. The heterocycle may be attached via any heteroatom or carbon atom. Heterocycles include heteroaryls as defined below. Examples of such heterocycles include, without limitation, morpholinyl, pyrrolidinonyl, pyrrolidinyl, piperidinyl, piperizynyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, tetrahydrothiopyranyl, and the like. Further heterocycles and heteroaryls are described in Katritzky et al., eds., Comprehensive Heterocyclic Chemistry: The Structure, Reactions, Synthesis and Use of Heterocyclic Compounds, Vol. 1-8, Pergamon Press, N.Y. (1984), which is hereby incorporated by reference in its entirety.

The term "acyl" refers to groups of from 1 to 8 carbon atoms of a straight, branched, or cyclic configuration, saturated, unsaturated, or aromatic, and combinations thereof, attached to the parent structure through a carbonyl functionality. One or more carbons in the acyl residue may be replaced by nitrogen, oxygen, or sulfur as long as the point of attachment to the parent remains at the carbonyl. Examples include acetyl (Ac), benzoyl, propionyl, isobutyryl, t-butoxycarbonyl, benzyloxycarbonyl, and the like.

The term "amino acid" refers to the fragment of an amino acid that remains following amide bond formation via reaction of the amino acid carboxyl group with an amino group of another molecule. The amino acid can be in D- or L-configuration. Suitable amino acids include α-amino acids, β-amino acids, γ-amino acids, δ-amino acids, and ε-amino acids, and include not only natural amino acids (i.e., those found in biological systems, including the twenty amino acids found in natural proteins), but also naturally-occurring variants of such amino acids, as well as synthetic amino acids and their analogues known to those skilled in the art. Exemplary amino acids include the twenty natural amino acids, 4-hydroxyproline, hydroxyysine, demosine, isodemosine, 3-methylhistidine, norvalin, beta-alanine, gamma-aminobutyric acid, citrulline, homocysteine, homoserine, ornithine, and methionine sulfone.

The term "pyrimidine" refers to a heteroaromatic compound containing a benzene ring with two carbon atoms replaced by two nitrogen atoms (diazine). For instance, the following moiety having the carbon atoms at positions 1 and 3 replaced by nitrogen atoms is considered a pyrimidine:

This term, as it is defined herein, also includes its isomeric forms of diazine, such as pyridazine, with the nitrogen atoms in positions 1 and 2; and pyrazine, with the nitrogen atoms in positions 1 and 4. The term "pyrimidine" also generally includes its analogues and derivatives. For instance, the natural nucleobases, cytosine (C), thymine (T), and uracil (U), are pyrimidine derivatives. The term "purine" refers to a heteroaromatic compound containing a pyrimidine ring fused to an imidazole ring. The term "purine" also generally includes its analogues and derivatives. For instance, the natural nucleobases, adenine (A) and guanine (G). Other examples of naturally occurring purine derivatives are hypoxanthine, xanthine, theobromine, caffeine, uric acid, and isoguanine. Exemplary purines and pyrimidines include those disclosed in U.S. Pat. No. 3,687,808; Concise Encyclopedia Of Polymer Science And Engineering, pages 858-859; Kroschwitz, J. I., ed. John Wiley & Sons, 1990; and Englisch et al., Angewandte Chemie, International Edition, 1991, 30, 613, each of which is hereby incorporated by reference in its entirety.

The term "nucleobase" includes all natural and synthetic nucleobases as well as universal nucleobases. Typical natural nucleobases include adenine, guanine, cytosine, uracil, and thymine. Synthetic nucleobases typically include inosine, xanthine, hypoxanthine, nubularine, isoguanisine, or tubercidine. As used herein, a universal nucleobase is any modified, unmodified, naturally occurring or non-naturally occurring nucleobase that can substitute for more than one of the natural nucleobases. Universal bases typically contain an aromatic ring moiety that may or may not contain nitrogen atoms and generally use aromatic ring stacking to stabilize an oligonucleotide duplex. Some universal bases can be covalently attached to the C-1' carbon of a pentose sugar to make a universal nucleotide. Some universal bases do not hydrogen bond specifically with another nucleobase. Some universal bases base pair with all of the naturally occurring nucleobases. Some universal bases may interact with adjacent nucleotide bases on the same nucleic acid strand by hydrophobic stacking Exemplary universal nucleobases include, but are not limited to, 2,4-difluorotoluene, nitropyrrolyl, nitroindolyl, 8-aza-7-deazaadenine, 4-fluoro-6-methylbenzimidazle, 4-methylbenzimidazle, 3-methyl isocarbostyrilyl, 5-methyl isocarbostyrilyl, 3-methyl-7-propynyl isocarbostyrilyl, 7-azaindolyl, 6-methyl-7-azaindolyl, imidizopyridinyl, 9-methyl-imidizopyridinyl, pyrrolopyrizinyl, isocarbostyrilyl, 7-propynyl isocarbostyrilyl, propynyl-7-azaindolyl, 2,4,5-trimethylphenyl, 4-methylinolyl, 4,6-dimethylindolyl, phenyl, napthalenyl, anthracenyl, phenanthracenyl, pyrenyl, stilbenzyl, tetracenyl, pentacenyl, and structural derivatives thereof.

Suitable nucleobases include, but are not limited to, 2-aminoadenine, 6-methyl and other alkyl derivatives of adenine and guanine, 2-propyl and other alkyl derivatives of adenine and guanine, 5-halouracil and cytosine, 5-propynyl uracil and cytosine, 6-azo uracil, cytosine and thymine, 5-uracil (pseudouracil), 4-thiouracil, 5-halouracil, 5-(2-aminopropyl)uracil, 5-amino allyl uracil, 8-halo, amino, thiol, thioalkyl, hydroxyl and other 8-substituted adenines and guanines, 5-trifluoromethyl and other 5-substituted uracils and cytosines, 7-methylguanine, 5-substituted pyrimidines, 6-azapyrimidines and N-2, N-6 and O-6 substituted purines, including 2-aminopropyladenine, 5-propynyluracil and 5-propynylcytosine, dihydrouracil, 3-deaza-5-azacytosine, 2-aminopurine, 5-alkyluracil, 7-alkylguanine, 5-alkyl cytosine, 7-deazaadenine, N6,N6-dimethyladenine, 2,6-diaminopurine, 5-amino-allyl-uracil, N3-methyluracil, substituted 1,2,4-triazoles, 2-pyridinone, 5-nitroindole, 3-nitropyrrole, 5-methoxyuracil, uracil-5-oxyacetic acid, 5-methoxycarbonylmethyluracil, 5-methyl-2-thiouracil, 5-methoxycarbonylmethyl-2-thiouracil, 5-methylaminomethyl-2-thiouracil, 3-(3-amino-3-carboxypropyl)uracil, 3-methylcytosine, 5-methylcytosine, N4-acetyl cytosine, 2-thiocytosine, N6-methyladenine, N6-isopentyladenine, 2-methylthio-N-6-isopentenyladenine, N-methylguanines, and O-alkylated bases. Further purines and pyrimidines include those disclosed in U.S. Pat. No. 3,687,808; Concise Encyclopedia Of Polymer Science And Engineering, pages 858-859; Kroschwitz, J. I., ed. John Wiley & Sons, 1990; and Englisch et al., Angewandte Chemie, International Edition, 1991, 30, 613, each of which is hereby incorporated by reference in its entirety.

The term "nucleoside" refers to a compound comprising a nucleobase, as defined herein, linked to a pentose at the 1'-position. When the nucleobase is a purine derivative or anologue, the pentose is typically attached to the nucleobase at the 9-position of the purine derivative or anologue. When the nucleobase is a pyrimidine derivative or anologue, the pentose is typically attached to the nucleobase at the 1-position of the pyrimidine (e.g., Kornberg and Baker, DNA Replication, 2nd Ed., Freeman, San Francisco, 1992, which is hereby incorporated by reference in its entirety). When a nucleoside is present in $R^3$, $R^4$, or $R^5$ herein, the nucleoside may be connected to the neighboring atom(s) through any atom on the nucleobase or pentose.

The term "fatty acid" generally refers to a carboxylic acid with an aliphatic tail (chain). The aliphatic chain can be between about 2 and about 36 carbon atoms in length. Fatty acids can be saturated, unsaturated, or polyunsaturated. The aliphatic chain can be a linear or a branched chain. The term "fatty acid" may be used herein to refer to a "fatty acid derivative" which can include one or more different fatty acid derivatives, or mixtures of fatty acids derivatives. Exemplary fatty acids include unsaturated fatty acids, saturated fatty acids, and diacids; mono-, di-, and tri-glycerides of ascarosides that have a carboxylic acid functionality; hydroxy acids, ω hydroxy acids, ω-1 hydroxy acids, di-hydroxy fatty acids (e.g., dihydroxy fatty acids that are omega- or omega-1 hydroxylated, as well as alpha- or beta-hydroxylated fatty acids).

The term "sugar" refers to a compound which is either a carbohydrate per se made up of one or more monosaccharide units having at least 5 carbon atoms (which may be linear, branched, or cyclic) with an oxygen, nitrogen, or sulfur atom bonded to each carbon atom; or a compound having as a part thereof a carbohydrate moiety made up of one or more monosaccharide units each having at least 5 carbon atoms (which may be linear, branched or cyclic), with an oxygen, nitrogen or sulfur atom bonded to each carbon atom. Representative sugars include the mono-, di-, tri-, and oligosaccharides containing from about 4-9 monosaccharide units, and polysaccharides such as starches, glycogen, cellulose, and polysaccharide gums. Exemplary monosaccharides include $C_5$ and above (e.g., $C_5$-$C_8$ or $C_5$-$C_6$) sugars; di- and trisaccharides include sugars having two or three monosaccharide units (e.g., $C_5$-$C_8$ or $C_5$-$C_8$).

The term "monosaccharide" means a sugar molecule having a chain of 3-10 carbon atoms in the form of an aldehyde (aldose) or ketone (ketose). Suitable monosaccharides include both naturally occurring and synthetic monosaccharides. Suitable monosaccharides include trioses, such as glycerone and dihydroxyacetone; textroses such as erythrose and erythrulose; pentoses, such as xylose, arabinose, ribose, xylulose ribulose; methyl pentoses (6-deoxyhexoses), such as rhamnose and fucose; hexoses, such as ascarylose, glucose, mannose, galactose, fructose, and sorbose; and heptoses, such as glucoheptose, galamannoheptose, sedoheptulose, and mannoheptulose. Exemplary monosaccharides embrace radicals of allose, altrose, arabinose, cladinose, erythrose, erythrulose, fructose, D-fucitol, L-fucitol, fucosamine, fucose, fuculose, galactosamine, D-galactosaminitol, N-acetyl-galactosamine, galactose, glucosamine, N-acetyl-glucosamine, glucosaminitol, glucose, glucose-6-phosphate, gulose glyceraldehyde, L-glycero-D-mannos-heptose, glycerol, glycerone, gulose, idose, lyxose, mannosamine, mannose, mannose-6-phosphate, psicose, quinovose, quinovasamine, rhamnitol, rhamnosamine, rhamnose, ribose, ribulose, sedoheptulose, sorbose, tagatose, talose, tartaric acid, threose, xylose, and xylulose. The monosaccharide can be in D- or L-configuration. A typical monosaccharide used herein is hexose.

The monosaccharide may further be a deoxy sugar (alcoholic hydroxy group replaced by hydrogen), amino sugar (alcoholic hydroxy group replaced by amino group), a thio sugar (alcoholic hydroxy group replaced by thiol, or C=O replaced by C=S, or a ring oxygen of cyclic form replaced by sulfur), a seleno sugar, a telluro sugar, an aza sugar (ring carbon replaced by nitrogen), an imino sugar (ring oxygen replaced by nitrogen), a phosphano sugar (ring oxygen replaced with phosphorus), a phospha sugar (ring carbon replaced with phosphorus), a C-substituted monosaccharide (hydrogen at a non-terminal carbon atom replaced with carbon), an unsaturated monosaccharide, an alditol (carbonyl group replaced with CHOH group), aldonic acid (aldehydic group replaced by carboxy group), a ketoaldonic acid, a uronic acid, an aldaric acid, and so forth. Amino sugars include amino monosaccharides, such as galactosamine, glucosamine, mannosamine, fucosamine, quinovasamine, neuraminic acid, muramic acid, lactosediamine, acosamine, bacillosamine, daunosamine, desosamine, forosamine, garosamine, kanosamine, kansosamine, mycaminose, mycosamine, perosamine, pneumosamine, purpurosamine, rhodosamine. It is understood that the monosaccharide and the like can be further substituted.

The terms "disaccharide", "trisaccharide", and "polysaccharide" embrace radicals of abequose, acrabose, amicetose, amylopectin, amylose, apiose, arcanose, ascarylose, ascorbic acid, boivinose, cellobiose, cellotriose, cellulose, chacotriose, chalcose, chitin, colitose, cyclodextrin, cymarose, dextrin, 2-deoxyribose, 2-deoxyglucose, diginose, digitalose, digitoxose, evalose, evernitrose, fructoologosachharide, galto-oligosaccharide, gentianose, gentiobiose, glucan, glucogen, glycogen, hamamelose, heparin, inulin, isolevoglucosenone, isomaltose, isomaltotriose, isopanose, kojibiose, lactose, lactosamine, lactosediamine, laminarabiose, levoglucosan, levoglucosenone, β-maltose, maltriose, mannan-oligosaccharide, manninotriose, melezitose, melibiose, muramic acid, mycarose, mycinose, neuraminic acid, nigerose, nojirimycin, moviose, oleandrose, panose, paratose, planteose, primeverose, raffinose, rhodinose, rutinose, sarmentose, sedoheptulose, solatriose, sophorose, stachyose, streptose, sucrose, α,α-trehalose, trehalosamine, turanose, tyvelose, xylobiose, umbelliferose, and the like. Further, it is understood that the "disaccharide", "trisaccharide", and "polysaccharide" and the like can be further substituted. Disaccharide also includes amino sugars and their derivatives, particularly, a mycaminose derivatized at the C-4' position or a 4 deoxy-3-amino-glucose derivatized at the C-6' position.

The term "polycyclic" or "multi-cyclic" used herein indicates a molecular structure having two or more rings, including, but not limited to, fused, bridged, or spiro rings.

The above "alkyl", "alkenyl", "cycloalkyl", and "cycloalkenyl" radicals, as well as the ring system of the above aryl, heterocyclyl, or heteroaryl groups, may be optionally substituted.

The term "substituted" or "optionally substituted" is used to indicate that a group may have a substituent at each substitutable atom of the group (including more than one substituent on a single atom), provided that the designated atom's normal valency is not exceeded and the identity of each substituent is independent of the others. In accordance with the present invention, up to three H atoms in each residue can be replaced with alkyl, halogen, haloalkyl, alkyenyl, haloalkenyl, cycloalkyl, cycloalkenyl, hydroxy, alkoxy, acyl, carboxy, carboalkoxy (also referred to as alkoxycarbonyl), carboxamido (also referred to as alkylaminocarbonyl), cyano, carbonyl, nitro, amino, alkylamino, dialkylamino, mercapto, alkylthio, sulfoxide, sulfone, acylamino, amidino, aryl, heteroaryl, heterocyclyl, aryloxy, heteroaryloxy, a purine or pyridimine or an analogue or derivative thereof (as defined in "nucleobase"), or a sugar such as a monosaccharide having 5 or 6 carbon atoms (as defined in "monosaccharide"). "Unsubstituted" atoms bear all of the hydrogen atoms dictated by their valency. When a substituent is keto (i.e., =O), then two hydrogens on the atom are replaced. Combinations of substituents and/or variables are permissible only if such combinations result in stable compounds; by "stable compound" or "stable structure" is meant a compound that is sufficiently robust to survive isolation to a useful degree of purity from a reaction mixture, and formulation into an efficacious agent.

In the characterization of some of the substituents, certain substituents may combine to form rings. Unless stated otherwise, it is intended that such rings may exhibit various degrees of unsaturation (from fully saturated to fully unsaturated), may include heteroatoms, and may be substituted with other substituent groups as described above.

The compounds described herein may contain one or more asymmetric centers and may thus give rise to enantiomers, diastereomers, and other stereoisomeric forms. Each chiral center may be defined, in terms of absolute stereochemistry, as (R)- or (S)-. The present invention is meant to include all such possible isomers, as well as mixtures thereof, including racemic and optically pure forms. Optically active (R)- and (S)-, (−)- and (+)-, or (D)- and (L)-isomers may be prepared using chiral synthons or chiral reagents, or resolved using conventional techniques. When the compounds described herein contain olefinic double bonds or other centers of geometric asymmetry, and unless specified otherwise, it is intended that the compounds include both E and Z geometric isomers. Likewise, all tautomeric forms are also intended to be included. The configuration of any carbon-carbon double bond appearing herein is selected for convenience only and is not intended to designate a particular configuration; thus a carbon-carbon double bond depicted arbitrarily herein as trans may be Z, E, or a mixture of the two in any proportion.

The term "compounds of the invention," and equivalent expressions, are meant to embrace the prodrugs, the pharmaceutically acceptable salts, the oxides, the solvates, e.g. hydrates, and inclusion complexes of that compound, where the context so permits, as well as any stereoisomeric form, or a mixture of any such forms of that compound in any ratio, unless otherwise specified. Inclusion complexes are described in Remington, The Science and Practice of Pharmacy, 19th Ed. 1:176-177 (1995), which is hereby incorporated by reference in its entirety. The most commonly employed inclusion complexes are those with cyclodextrins, and all cyclodextrin complexes, natural and synthetic, are specifically encompassed within the claims. Thus, in accordance with some embodiments of the invention, a compound as described herein, including in the contexts of pharmaceutical compositions, methods of treatment, and compounds per se, is provided as the salt form. Similarly, reference to intermediates, whether or not they themselves are claimed, is meant to embrace their salts, and solvates, where the context so permits. For the sake of clarity, particular instances when the context so permits are sometimes indicated in the text, but these instances are purely illustrative and it is not intended to exclude other instances when the context so permits.

The "quaternization" of any basic nitrogen-containing groups of the compounds disclosed herein is also contemplated. The basic nitrogen can be quaternized with any agents known to those of ordinary skill in the art including, for example, lower alkyl halides, such as methyl, ethyl, propyl and butyl chloride, bromides and iodides; dialkyl sulfates including dimethyl, diethyl, dibutyl and diamyl sulfates; long chain halides such as decyl, lauryl, myristyl and stearyl chlorides, bromides and iodides; and aralkyl halides including benzyl and phenethyl bromides. Water or oil-soluble or dispersible products may be obtained by such quaternization.

As used herein, the term "ascaroside" refers to a compound of Formula I:

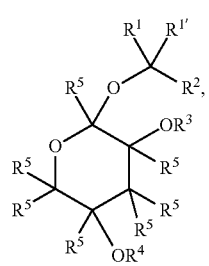

(Formula I)

or a pharmaceutical equivalent, derivative, analog, and/or salt thereof. As readily apparent to one of skill in the art, the compound may be further defined by various R groups. For example, in accordance with an embodiment herein, $R^2$ may contain the moiety of the formula:

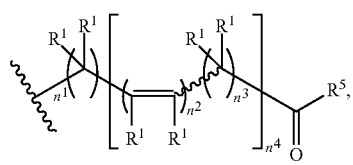

(Formula II)

or a pharmaceutical equivalent, derivative, analog and/or salt thereof.

As used herein, the term "ascr" and the designated # refers to varieties of ascarosides and ascaroside-like compounds. For example, ascr#1 is a compound described herein as a Formula III:

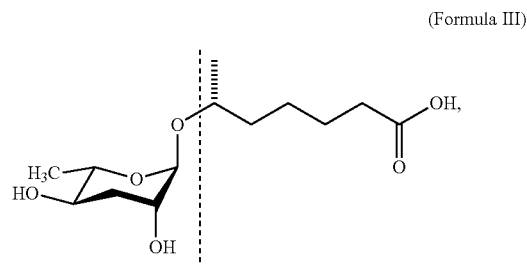

(Formula III)

or a pharmaceutical equivalent, derivative, analog and/or salt thereof.

As disclosed herein, the inventors performed a liquid chromatography mass spectrometric screen for ascarosides in 21 different nematode species, both free-living and parasitic. It was found that many species produce species-specific but partially overlapping blends of ascarosides, indicating that ascarosides are highly conserved among nematodes. The inventors found that many nematodes also respond to ascarosides through attraction or repulsion, presenting possible new targets for the control of parasites. Additionally, as disclosed herein, the inventors also investigated the effect of ascarosides on a mouse asthma model. They found that administration of ascaroside compounds, specifically administration of ascr#1, ascr#3 and ascr#7, which was produced in *Nippostrongylus brasiliensis*, resulted in a reduction of eosinophils, decreased cellular infiltration and decreased mucus hyper-production in asthmatic mice.

In one embodiment, the present invention provides a method of treating, alleviating and/or preventing a disorder in a subject by administering a composition comprising a therapeutically effective dosage of a compound of Formula I:

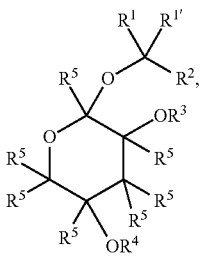

(Formula I)

or a pharmaceutical equivalent, derivative, analog, and/or salt thereof. In another embodiment, the disorder is an inflammatory and/or immune disorder. In another embodiment, the disorder is *acne vulgaris*, asthma, autoimmune diseases, celiac disease, chronic prostatitis, glomerulonephritis, Hypersensitivities, Inflammatory bowel diseases, pelvic inflammatory disease, reperfusion injury, rheumatoid arthritis, sarcoidosis, transplant rejection, vasculitis, Interstitial cystitis, lupus, *scleroderma*, certain types of hemolytic anemia, type one diabetes, graves disease, multiple sclerosis, Goodpasture's syndrome, pernicious anemia, some types of myopathy, seasonal allergy, mastocytosis, perennial allergy, anaphylaxis, food allergy, allergic rhinitis, atopic dermatitis, and/or autism. In another embodiment, the composition is administered orally. In another embodiment, the composition is administered by direct injection and/or intravenously. In another embodiment, the subject is a human. In another embodiment, the subject is a rodent. In another embodiment, the subject is selected from the group consisting of primates, equines, horses, cattle, cows, swine, sheep, rats, pets, cats, dogs and guinea pigs.

In another embodiment, the present invention provides a composition comprising a therapeutically effective dosage of a compound of Formula I:

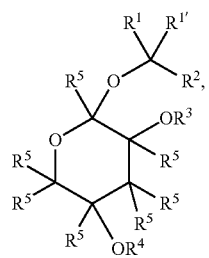

(Formula I)

or a pharmaceutical equivalent, derivative, analog, and/or salt thereof, and a pharmaceutically acceptable carrier. In another embodiment, the composition comprises a blend of ascr#1, ascr#3 and/or ascr#7.

In accordance with various embodiments herein, additional compounds designated as R groups may further define the compound of Formula I:

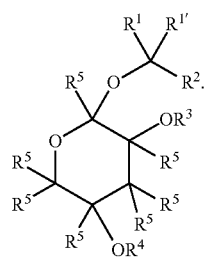

(Formula I)

Various embodiments include where:

$R^1$ is H, —C(R)$_3$, —OR, —N(R)$_2$, halogen, an alkyl, a haloalkyl, an alkenyl, or a haloalkenyl; where each R is independently H, halogen, an alkyl, or an alkenyl;

$R^{1'}$ is absent, H, —C(R)$_3$, —OR, —N(R)$_2$, halogen, an alkyl, a haloalkyl, an alkenyl, or a haloalkenyl; where each R is independently H, halogen, an alkyl, or an alkenyl;

$R^2$ is a moiety of formula

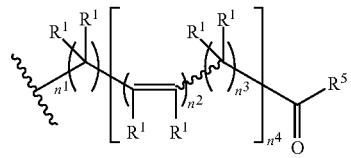

where:
each $R^1$ is independently H, —C(R)$_3$, —OR, —N(R)$_2$, halogen, an alkyl, a haloalkyl, an alkenyl, or a haloalkenyl; where each R is independently H, halogen, an alkyl, or an alkenyl;

$R^5$ is H, —OH, —OR$^6$, —OCR$^6$R$^7$R$^8$, —CR$^6$R$^7$R$^8$, —NH$_2$, —NHR$^6$, —NR$^6$R$^7$, halogen, an alkyl, a haloalkyl, an alkenyl, a haloalkenyl, an aryl, a heteroaryl, an arylalkyl, a heterocyclyl, a cycloalkyl, a cycloalkenyl, an acyl, an amino acid, a nucleoside, a monosaccharide having 5 or 6 carbon atoms, or a bond connecting to $R^3$ or $R^4$ of another unit of Formula I;

where:
$R^6$ and $R^7$ are each independently H, —CR$_3$, —OR, —N(R)$_2$, halogen, an alkyl, a haloalkyl, an alkenyl, a haloalkenyl, an aryl, a heteroaryl, a heterocyclyl, a cycloalkyl, or a cycloalkenyl, where the alkyl, alkenyl, aryl, heteroaryl, heterocyclyl, cycloalkyl, or cycloalkenyl is optionally substituted with one or more substituents independently selected from the group consisting of —OR$^8$, —C(O)R$^8$, —NHC(O)R$^8$, an alkyl, a haloalkyl, an aryl, a heteroaryl, a heterocyclyl, and a cycloalkyl;

where:
each R is independently H, halogen, an alkyl, or an alkenyl; and $R^8$ is H, —C(R)$_3$, —[C(R)$_2$]$_{n4}$NHC(O)R$^9$, —[C(R)$_2$]$_{n4}$C(O)(NH)R$^9$, —OR, —N(R)$_2$, halogen, an alkyl, a haloalkyl, an alkenyl, a haloalkenyl, an aryl, a heteroaryl, a heterocyclyl, a cycloalkyl, a cycloalkenyl, a purine, a pyrimidine, or a monosaccharide having 5 or 6 carbon atoms, where the alkyl, alkenyl, aryl, heteroaryl, heterocyclyl, cycloalkyl, cycloalkenyl, purine, pyrimidine, or monosaccharide is optionally substituted with one or more substituents independently selected from the group consisting of —C(R)$_3$, —OR$^9$, —C(O)R$^9$, —NHC(O)R$^9$, halogen, an alkyl, a haloalkyl, an aryl, a heteroaryl, a heterocyclyl, a cycloalkyl, and a monosaccharide having 5 or 6 carbon atoms;

where:
each R is independently H, halogen, an alkyl, or an alkenyl; $R^9$ is H, —C(R)$_3$, —OR, —N(R)$_2$, halogen, an alkyl, a haloalkyl, an alkenyl, a haloalkenyl, an aryl, a heteroaryl, a heterocyclyl, a cycloalkyl, a cycloalkenyl, a purine, a pyrimidine, or a monosaccharide having 5 or 6 carbon atoms, where the alkyl, alkenyl, aryl, heteroaryl, heterocyclyl, cycloalkyl, cycloalkenyl, purine, pyrimidine, or monosaccharide is optionally substituted with one or more substituents independently selected from the group consisting of —C(R)$_3$, —OR, —C(O)R, halogen, an alkyl, a haloalkyl, an aryl, a heteroaryl, a heterocyclyl, and a cycloalkyl; where each R is independently H, halogen, an alkyl, or an alkenyl; and $n^4$ n is an integer of 1 to 30; and $R^8$ is H, —C(R)$_3$, —[C(R)$_2$]$_{n4}$NHC(O)R$^9$, —[C(R)$_2$]$_{n4}$C(O)(NH)R$^9$, —OR, —N(R)$_2$, halogen, an alkyl, a haloalkyl, an alkenyl, a haloalkenyl, an aryl, a heteroaryl, a heterocyclyl, a cycloalkyl, a cycloalkenyl, a purine, a pyrimidine, or a monosaccharide having 5 or 6 carbon atoms, where the alkyl, alkenyl, aryl, heteroaryl, heterocyclyl, cycloalkyl, cycloalkenyl, purine, pyrimidine, or monosaccharide is optionally substituted with one or more substituents independently selected from the group consisting of —C(R)$_3$, —OR$^9$, —C(O)R$^9$, —NHC(O)R$^9$, halogen, an alkyl, a haloalkyl, an aryl, a heteroaryl, a heterocyclyl, a cycloalkyl, and a monosaccharide having 5 or 6 carbon atoms;

where:
  each R is independently H, halogen, an alkyl, or an alkenyl;
  $R^9$ is H, —$C(R)_3$, —OR, —$N(R)_2$, halogen, an alkyl, a haloalkyl, an alkenyl, a haloalkenyl, an aryl, a heteroaryl, a heterocyclyl, a cycloalkyl, a cycloalkenyl, a purine, a pyrimidine, or a monosaccharide having 5 or 6 carbon atoms, where the alkyl, alkenyl, aryl, heteroaryl, heterocyclyl, cycloalkyl, cycloalkenyl, purine, pyrimidine, or monosaccharide is optionally substituted with one or more substituents independently selected from the group consisting of —$C(R)_3$, —OR, —C(O)R, halogen, an alkyl, a haloalkyl, an aryl, a heteroaryl, a heterocyclyl, and a cycloalkyl; where each R is independently H, halogen, an alkyl, or an alkenyl; and
  $n^4$ is an integer of 1 to 30;
$n^1$, $n^2$, and $n^3$ are each independently an integer of 0 to 30;
$n^4$ is an integer of 1 to 30; and
the sum of $n^1$, each $n^2$, and each $n^3$ is 1 to 30;
$R^3$ and $R^4$ are each independently H, —$CR^6R^7R^8$, —$C(O)R^8$, an alkyl, a haloalkyl, an alkenyl, a haloalkenyl, an aryl, a heteroaryl, a heterocyclyl, a cycloalkyl, a cycloalkenyl, an acyl, an amino acid, a nucleoside, a monosaccharide having 5 or 6 carbon atoms, or a bond connecting to $R^5$ of another unit of Formula I; where:
  $R^6$ and $R^7$ are each independently H, —$CR_3$, —OR, —$N(R)_2$, halogen, an alkyl, a haloalkyl, an alkenyl, a haloalkenyl, an aryl, a heteroaryl, a heterocyclyl, a cycloalkyl, or a cycloalkenyl, where the alkyl, alkenyl, aryl, heteroaryl, heterocyclyl, cycloalkyl, or cycloalkenyl is optionally substituted with one or more substituents independently selected from the group consisting of —$OR^8$, —$C(O)R^8$, —$NHC(O)R^8$, an alkyl, a haloalkyl, an aryl, a heteroaryl, a heterocyclyl, and a cycloalkyl;
  where:
    each R is independently H, halogen, an alkyl, or an alkenyl; and
    $R^8$ is H, —$C(R)_3$, —$[C(R)_2]_{n4}NHC(O)R^9$, —$[C(R)_2]_{n4}C(O)(NH)R^9$, —OR, —$N(R)_2$, halogen, an alkyl, a haloalkyl, an alkenyl, a haloalkenyl, an aryl, a heteroaryl, a heterocyclyl, a cycloalkyl, a cycloalkenyl, a purine, a pyrimidine, or a monosaccharide having 5 or 6 carbon atoms, where the alkyl, alkenyl, aryl, heteroaryl, heterocyclyl, cycloalkyl, cycloalkenyl, purine, pyrimidine, or monosaccharide is optionally substituted with one or more substituents independently selected from the group consisting of —$C(R)_3$, —$OR^9$, —$C(O)R^9$, —$NHC(O)R^9$, halogen, an alkyl, a haloalkyl, an aryl, a heteroaryl, a heterocyclyl, a cycloalkyl, and a monosaccharide having 5 or 6 carbon atoms;
    where:
      each R is independently H, halogen, an alkyl, or an alkenyl; $R^9$ is H, —$C(R)_3$, —OR, —$N(R)_2$, halogen, an alkyl, a haloalkyl, an alkenyl, a haloalkenyl, an aryl, a heteroaryl, a heterocyclyl, a cycloalkyl, a cycloalkenyl, a purine, a pyrimidine, or a monosaccharide having 5 or 6 carbon atoms, where the alkyl, alkenyl, aryl, heteroaryl, heterocyclyl, cycloalkyl, cycloalkenyl, purine, pyrimidine, or monosaccharide is optionally substituted with one or more substituents independently selected from the group consisting of —$C(R)_3$, —OR, —C(O)R, halogen, an alkyl, a haloalkyl, an aryl, a heteroaryl, a heterocyclyl, and a cycloalkyl; where each R is independently H, halogen, an alkyl, or an alkenyl; and
      $n^4$ is an integer of 1 to 30; and
  $R^8$ is H, —$C(R)_3$, —$[C(R)_2]_{n4}NHC(O)R^9$, —$[C(R)_2]_{n4}C(O)(NH)R^9$, —OR, —$N(R)_2$, halogen, an alkyl, a haloalkyl, an alkenyl, a haloalkenyl, an aryl, a heteroaryl, a heterocyclyl, a cycloalkyl, a cycloalkenyl, a purine, a pyrimidine, or a monosaccharide having 5 or 6 carbon atoms, where the alkyl, alkenyl, aryl, heteroaryl, heterocyclyl, cycloalkyl, cycloalkenyl, purine, pyrimidine, or monosaccharide is optionally substituted with one or more substituents independently selected from the group consisting of —$C(R)_3$, —$OR^9$, —$C(O)R^9$, —$NHC(O)R^9$, halogen, an alkyl, a haloalkyl, an aryl, a heteroaryl, a heterocyclyl, and a cycloalkyl;
  where each R is independently H, halogen, an alkyl, or an alkenyl; and
  $n^4$ is an integer of 1 to 30; and
each $R^5$ is independently H, —OH, —$OR^6$, —$OCR^6R^7R^8$, —$CR^6R^7R^8$, —$NH_2$, —$NHR^6$, —$NR^6R^7$, halogen, an alkyl, a haloalkyl, an alkenyl, a haloalkenyl, an aryl, a heteroaryl, an arylalkyl, a heterocyclyl, a cycloalkyl, a cycloalkenyl, an acyl, an amino acid, a nucleoside, a monosaccharide having 5 or 6 carbon atoms, or a bond connecting to $R^3$ or $R^4$ of another unit of Formula I;
where:
  $R^6$ and $R^7$ are each independently H, —$CR_3$, —OR, —$N(R)_2$, halogen, an alkyl, a haloalkyl, an alkenyl, a haloalkenyl, an aryl, a heteroaryl, a heterocyclyl, a cycloalkyl, or a cycloalkenyl, where the alkyl, alkenyl, aryl, heteroaryl, heterocyclyl, cycloalkyl, or cycloalkenyl is optionally substituted with one or more substituents independently selected from the group consisting of —$OR^8$, —$C(O)R^8$, —$NHC(O)R^8$, an alkyl, a haloalkyl, an aryl, a heteroaryl, a heterocyclyl, and a cycloalkyl;
  where:
    each R is independently H, halogen, an alkyl, or an alkenyl; and
    $R^8$ is H, —$C(R)_3$, —$[C(R)_2]_{n4}NHC(O)R^9$, —$[C(R)_2]_{n4}C(O)(NH)R^9$, —OR, —$N(R)_2$, halogen, an alkyl, a haloalkyl, an alkenyl, a haloalkenyl, an aryl, a heteroaryl, a heterocyclyl, a cycloalkyl, a cycloalkenyl, a purine, a pyrimidine, or a monosaccharide having 5 or 6 carbon atoms, where the alkyl, alkenyl, aryl, heteroaryl, heterocyclyl, cycloalkyl, cycloalkenyl, purine, pyrimidine, or monosaccharide is optionally substituted with one or more substituents independently selected from the group consisting of —$C(R)_3$, —$OR^9$, —$C(O)R^9$, —$NHC(O)R^9$, halogen, an alkyl, a haloalkyl, an aryl, a heteroaryl, a heterocyclyl, a cycloalkyl, and a monosaccharide having 5 or 6 carbon atoms;
where:
each R is independently H, halogen, an alkyl, or an alkenyl;
$R^9$ is H, —$C(R)_3$, —OR, —$N(R)_2$, halogen, an alkyl, a haloalkyl, an alkenyl, a haloalkenyl, an aryl, a heteroaryl, a heterocyclyl, a cycloalkyl, a cycloalkenyl, a purine, a pyrimidine, or a monosaccharide having 5 or 6 carbon atoms, where the alkyl, alkenyl, aryl, heteroaryl, heterocyclyl, cycloalkyl, cycloalkenyl, purine, pyrimidine, or monosaccharide is optionally substituted with one or more substituents independently selected from the group consisting of —$C(R)_3$, —OR, —C(O)R, halogen, an alkyl, a haloalkyl, an aryl, a heteroaryl, a heterocyclyl, and a cycloalkyl; where each R is independently H, halogen, an alkyl, or an alkenyl; and
$n^4$ is an integer of 1 to 30; and
$R^8$ is H, —$C(R)_3$, —$[C(R)_2]_{n4}NHC(O)R^9$, —$[C(R)_2]_{n4}C(O)(NH)R^9$, —OR, —$N(R)_2$, halogen, an alkyl, a haloalkyl, an alkenyl, a haloalkenyl, an aryl, a heteroaryl, a heterocyclyl, a cycloalkyl, a cycloalkenyl, a purine, a pyrimidine, or a monosaccharide having 5 or 6 carbon atoms, where the alkyl, alkenyl, aryl, heteroaryl, heterocyclyl, cycloalkyl, cycloalkenyl, purine, pyrimidine, or monosaccharide is optionally substituted with one or more substituents independently selected from the group consisting of —$C(R)_3$, —$OR^9$, —$C(O)R^9$, —$NHC(O)R^9$, halogen, an alkyl, a haloalkyl, an aryl, a heteroaryl, a heterocyclyl, a cycloalkyl, and a monosaccharide having 5 or 6 carbon atoms;
where:
each R is independently H, halogen, an alkyl, or an alkenyl;
$R^9$ is H, —$C(R)_3$, —OR, —$N(R)_2$, halogen, an alkyl, a haloalkyl, an alkenyl, a haloalkenyl, an aryl, a heteroaryl, a heterocyclyl, a cycloalkyl, a cycloalkenyl, a purine, a pyrimidine, or a monosaccharide having 5 or 6 carbon atoms, where the alkyl, alkenyl, aryl, heteroaryl, heterocyclyl, cycloalkyl, cycloalkenyl, purine, pyrimidine, or monosaccharide is optionally substituted with one or more substituents independently selected from the group consisting of —$C(R)_3$, —OR, —C(O)R, halogen, an alkyl, a haloalkyl, an aryl, a heteroaryl, a heterocyclyl, and a cycloalkyl; where each R is independently H, halogen, an alkyl, or an alkenyl; and
$n^4$ is an integer of 1 to 30; or
(ii) a compound comprising:
at least one nucleobase,
at least one fatty acid,
at least one amino acid, and
at least one sugar;
where the at least one nucleobase, the at least one fatty acid, the at least one amino acid, and the at least one sugar are linked by covalent bonds; and
where the compound has a molecular weight of less than about 2,000 g/mol.
In at least one embodiment of this aspect of the present invention, the one or more modulator compounds is a compound of Formula I. Suitable modulator compounds according to this embodiment include one or more isolated modulator compounds of Formula I' or Formula I":

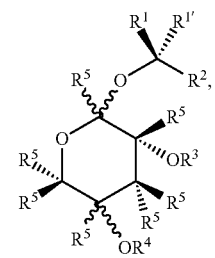

I'

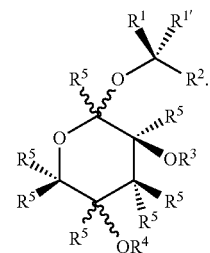

I"

Suitable modulator compounds according to this embodiment also include one or more isolated modulator compounds of Formula I in which at least one of the following conditions is met:
(i) $R^1$ is independently —$C(R')_3$, —OR, —$N(R)_2$, halogen, a haloalkyl, an alkenyl, or a haloalkenyl; wherein each R is independently H, halogen, an alkyl, or an alkenyl, and each R' is independently halogen or an alkenyl; and
$R^{1'}$ is independently absent, H, —$C(R)_3$, —OR, —$N(R)_2$, halogen, an alkyl, a haloalkyl, an alkenyl, or a haloalkenyl;
(ii) $R^2$ is

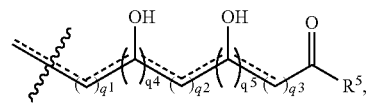

wherein:
each ----- is independently a single or double bond;
$q^1$, $q^2$, and $q^3$ are each independently an integer of 1 to 26;
$q^4$ and $q^5$ are each independently an integer of 0 to 26;
the sum of $q^1$, $q^2$, $q^3$, $q^4$, and $q^5$ is less than or equal to 28; and
the sum of $q^4$ and $q^5$ is greater than or equal to 2;
(iii) $R^5$ is H, —$OR^6$, —$OCR^6R^7R^8$, —$CR^6R^7R^8$, —$NH_2$, —$NR^6R^7$, halogen, a haloalkyl, an alkenyl, a haloalkenyl, an aryl, a heteroaryl, an arylalkyl, a heterocyclyl, a cycloalkyl, a cycloalkenyl, an acyl, an amino acid, or a nucleoside;
(iv) $R^5$ is a bond connecting to $R^3$ or $R^4$ of another unit of Formula I, forming a compound containing at least two units of Formula I;
(v) $R^3$ and $R^4$ are each independently —$CR^6R^7R^8$, a haloalkyl, an alkenyl, a haloalkenyl, an aryl, a heteroaryl, a heterocyclyl, a cycloalkyl, a cycloalkenyl, an acyl, an amino acid, a nucleoside, or —$(CO)R^8$ wherein $R^8$ is H, —$C(R)_3$, —$[C(R)_2]_{n4}NHC(O)R^9$, —$[C(R)_2]_{n4}C(O)(NH)R^9$, —OR, —$N(R)_2$, halogen, an alkyl, a haloalkyl, a cycloalkyl, a cycloalkenyl, a purine, a pyrimidine, or a monosaccharide having 5 or 6 carbon atoms, wherein the alkyl, cycloalkyl, cycloalkenyl, purine, pyrimidine, or monosaccharide is optionally substituted with one or more substituents independently selected from the group consisting of —C(R)$_3$, —OR$^9$, —C(O)R$^9$, —NHC(O)R$^9$, halogen, an alkyl, a haloalkyl, an aryl, a heteroaryl, a heterocyclyl, a cycloalkyl, and a monosaccharide having 5 or 6 carbon atoms;

(vi) the compound is a compound of Formula I";

with the proviso that the compound is not

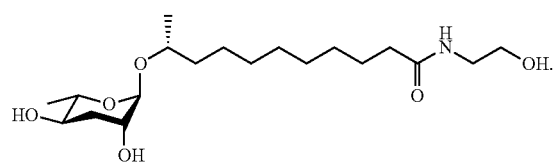

In at least one embodiment of this aspect of the present invention, the one or more modulator compounds is a compound comprising at least one nucleobase, at least one fatty acid, at least one amino acid, and at least one sugar.

In this and all aspects of the present invention, a single modulator compound or a combination of modulator compounds can be administered.

In various aspects of the present invention, ascarosides may be produced by a nematode. The nematode may include Acuarioidea, *Aelurostrongylus, Aelurostrongylus abstrusus*, Amidostomatidae, *Amidostomum, Ancylostoma braziliense, Ancylostoma caninum* (dog hookworm), *Ancylostoma ceylanicum, Ancylostoma duodenale, Ancylostoma tubaeforme*, Ancylostomatidae, Ancylostomatinae, Angiostrongylidae, *Angiostrongylus*, Aproctoidea, *Ascaridia galli, Ascaris lumbricoidies, Ascaris suum*, Brevistriatinae, *Brugia malayi, Brugia timori*, Bunostominae, Camallanoidea, *Carolinensis minutus, Chabertia, Chabertia ovina*, Chabertiidae, *Cloacina*, Cloacinidae, *Cooperia, Cooperia pectinata, Cooperia punctata*, Cooperiidae, Cosmocercoidea, *Crenosoma*, Crenosomatidae, *Cyathostoma*, Cyathostominae, *Cyclodontostomum, Cylicocyclus nassatus, Cystocaulus, Cystocaulus ocreatus*, Deletrocephalidae, Deletrocephalus, Diaphanocephalidae, Diaphanocephaloidea, Dictyocaulidae, Dictyocaulinae, *Dictyocaulus arnfeldi, Dictyocaulus filaria, Dictyocaulus osleri, Dictyocaulus viviparus, Dictyocausus viviparous, Didelphostrongylus, Dioctophyma renale*, Dioctophymatoidea, Diplotriaenoidea, *Dirofilaria immitis*, Dracunculoidea, Dromaeostrongylidae, *Elaeophora scheideri*, Elaphostrongylinae, *Filarinema*, Filarioidea, *Filaroides*, Filaroididae, Gapeworm, Ghathostomatoidea, Globocephaloidinae, *Gongylonema pulchrum*, Gyalocephalinae, *Habronema*, Habronematoidea, Haemonchidae, Haemonchinae, *Haemonchus contortus, Haemonchus placei, Halocercus*, Heligmonellidae, Heligmonellinae, *Heligmonoides speciosus*, Heligmosomatidae, Heligmosomidae, Heligmosomoidea, Heligmosomoides, Herpetostrongylidae, Herpetostrongylinae, Heterakoidea, *Hovorkonema, Hypodontus, Kalicephalus, Labiomultiplex, Labiosimplex, Labiostrongylus*, Libyostrongylinae, *Loa loa, Longistriata*, Mackerrastrongylidae, *Macroponema, Macropostrongylus, Mansonella ozzardi, Mansonella perstans, Mansonella streptocerca, Marshallagia*, Metastrongylidae, Metastrongyloidea (lungworms), Metastrongyloidea sp. RJ-2010, *Metastrongylus, Metastrongylus apri, Metastrongylus asymmetricus, Metastrongylus confusus, Metastrongylus elongates, Metastrongylus pudendotectus, Metastrongylus salmi*, Molineidae, Molineoidea, *Monilonema*, Muellerinae, *Muellerius capillaris*, Muspiceoidea, Nematodirinae, *Nematodirus battus, Neoheligmonella granjoni, Nicollina*, Nicollinidae, Nippostrongylinae, *Nippostrongylus brasiliensis, Oesophagostomum, Oesophagostomum columbianum, Oesophagostomum radiatum, Ohbayashinema, Oncocerca volvulus, Orientostrongylus ezoensis, Oslerus, Oslerus osleri, Ostertagia ostertagi, Ostertagia venulosum, Otostrongylus, Oxyurodiea, Papillostrongylus, Paraelaphostronyglus tenuis*, Parafilaroides, *Parazoniolaimus*, Physalopteroidea, *Potorostrongylus*, Protostrongylidae, Protostrongylinae, Pseudaliidae, *Pseudalius*, Rictularioidea, *Rugopharynx, Setaria cervi*, Seuratoidea, *Skrjabingylus*, Spiruroidea, *Stenurus, Stephanofilaria stilesi*, Stephanuridae, *Stephanurus, Strongylida, Strongylida* sp. AM-2008, Strongylidae, Strongylinae, Strongyloidea, *Strongyloides papillosus*, Subuluroidea, Syngamidae, *Syngamus, Teladorsagia circumcincta, Ternidens, Tetrabothriostrongylus*, Thelazioidea, *Torynurus, Toxocana canis, Toxocara cati, Toxocara vitulorum, Trichinella spiralis*, Trichinelloidea, *Trichostronglyus axei, Trichostronglyus colubriformis, Trichostronglyus vitrinus*, Trichostrongylidae, Trichostrongylinae, Trichostrongyloidea, *Trichuris suis, Troglostrongylus, Umingmakstrongylus pallikuukensis*, Unclassified Metastrongyloidea, unclassified Protostrongylidae, unclassified *Strongylida*, unclassified Trichostrongylidae, Varestrongylinae, *Wucheria bancrofti*, and *Zoniolaimus*. Other suitable nematodes according to this aspect of the present invention include Amidostomatidae, Ancylostomatidae, Angiostrongylidae, Brevistriatinae, Chabertiidae, Cloacinidae, Cooperiidae, Crenosomatidae, Deletrocephalidae, Diaphanocephalidae, Dictyocaulidae, Filaroididae, Haemonchidae, Heligmonellidae, Heligmosomatidae, Heligmosomidae, Herpetostrongylidae, Mackerrastrongylidae, Metastrongylidae, Molineidae, Nicollinidae, Oxyurodidea, Parafilaroidea, Protostrongylidae, Pseudaliidae, Stephanuridae, Strongylidae, Syngamidae, Trichostrongylidae, Ancylostomatinae, Brevistriatinae, Bunostominae, Cyathostominae, Dictyocaulinae, Gyalocephalinae, Haemonchinae, Heligmonellinae, Herpetostrongylinae, Libyostrongylinae, Muellerinae, Nematodirinae, Nippostrongylinae, Protostrongylinae, Strongylinae, Trichostrongylinae, Varestrongylinae, Acuarioidea, Aproctoidea, Camallanoidea, Cosmocercoidea, Diaphanocephaloidea, Dioctophymatoidea, Diplotriaenoidea, Dracunculoidea, Filarioidea, Ghathostomatoidea, Habronematoidea, Heligmosomoidea, Heterakoidea, Metastrongyloidea, Molineoidea, Muspiceoidea, Physalopteroidea, Rictularioidea, Seuratoidea, Spiruroidea, Strongyloidea, Subuluroidea, Thelazioidea, Trichinelloidea, Trichostrongyloidea, Metastrongyloidea, Protostrongylidae, Strongylidae, Trichostrongylidae, *Aelurostrongylusabstrusus, Amidostomumanseris, Ancylostomabraziliense, Ancylostomacaninum, Ancylostomaceylanicum, Ancylostomaduodenale, Ancylostomatubaeforme, Angiostrongyluscantonensis, Ascaridiagalli, Ascarislumbricoidies, Ascarissuum, Bolbosomacapitatum, Brugiamalayi, Brugiatimori, Bunostomumphlembotomum, Capillariabovis, Carolinensisminutus, Chabertiaovina, Cloacina* sp., *Cooperiapectinata, Cooperiapunctata, Cooperia* spp., *Crassicaudaboopis, Crenosoma* sp., *Cyathostoma* sp., *Cyathostomumcatinatum, Cyathostomumcoronatum, Cyclodontostomum, Cylicocyclusnassatus, Cylicostephanuscalicatus, Cylicostephanusgoldi, Cylicostephanuslongibursatus, Cystocaulus* sp., *Cystocaulusocreatus, Deletrocephalus* sp., *Dictyocaulusarnfeldi, Dictyocaulusfilaria, Dictyocaulusosleri, Dictyocaulusviviparus, Dictyocausus viviparous, Didelphostrongylus, Dioctophymarenale, Dirofilariaimmitis, Dracucunculusmedinensis*, Dromaeostrongylidae, *Elaeophorascheideri*, Elaphostrongylinae, *Enterobiusver-*

*micularis, Filarinema* sp., *Filaroides* sp., Globocephaloidinae, *Globoderapallida, Gnathostomadoloresi, Gongylonemapulchrum, Habronema* sp., *Haemonchuscontortus, Haemonchusplacei, Halocercus* sp., *Heligmonoidesspeciosus, Heligmosomoides* sp., *Heligmosomoidespolygyrus, Hovorkonema* sp., *Hypodontus* sp., *Kalicephalus* sp., *Labiomultiplex* sp., *Labiosimplex* sp., *Labiostrongylus* sp., *Loa boa, Longistriata* sp., *Macroponema* sp., *Macropostrongylus, Mansonella ozzardi, Mansonella perstans, Mansonella streptocerca, Marshallagiasp., Metastrongyloidea* sp. RJ-2010, *Metastrongylus* sp., *Metastrongylusapri, Metastrongylus asymmetricus, Metastrongylus confusus, Metastrongylus elongates, Metastrongybu spudendotectus, Metastrongybussabmi, Monilonema* sp., *Muebberiuscapibbaris, Necator americanus, Nematodirusbattus, Nematodirus helvetianus, Neoheligmonella granjoni, Nicollina* sp., *Nippostrongybus brasiliensis, Oesophagostomum* sp., *Oesophagostomumcolumbianum, Oesophagostomumradiatum, Oesophatostomumdentatum, Ohbayashinema* sp., *Onchocerca volvulus, Orientostrongylusezoensis, Oslerus* sp., *Oslerusosleri, Ostertagiabisonis, Ostertagiaostertagi, Ostertagiaostertagi, Ostertagiavenulosum, Otostrongylus, Papillostrongylus* sp., *Paraelaphostronyglus tenuis, Parazoniolaimus* sp., *Placentonema gigantissima, Potorostrongylus* sp., *Pseudalius* sp., *Rugopharynx* sp., *Setariacervi, Skrjabingylus* sp., *Stenurus* sp., *Stephanofilariastilesi, Stephanurus* sp., *Strongylida* sp. AM-2008, *Strongyloides papillosus, Strongyloides ratti, Strongyloides venezuelensis, Syngamus trachea, Teladorsagia* sp., *Teladorsagia circumcincta, Ternidens* sp., *Tetrabothriostrongylus* sp., *Torynurus* sp., *Toxocanacanis, Toxocaracati, Toxocaravitulorum, Trichinellabritovi, Trichinellamurrelli, Trichinellanativa, Trichinella nelsoni, Trichinella papuae, Trichinella pseudospiralis, Trichinella spiralis, Trichinella zimbabwensis, Trichostronglyus axei, Trichostronglyus colubriformis, Trichostronglyus vitrinus, Trichostrongylus axei, Trichuris discolor, Trichuris muris, Trichuris suis, Trichuris trichiura, Troglostrongylus, Umingmakstrongylus pallikuukensis, Uncinariastenocephala, Wucheria bancrofti*, and *Zoniolaimus* sp.

EXAMPLES

The following example is provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

Example 1

Generally

Nematodes cause significant human disease and agricultural damage. Interfering with chemically-mediated nematode behaviors could potentially prevent or mitigate nematode infections. Two chemically distinct mate-finding cues have been reported in nematodes: vanillic acid in *Heterodera glycines* and several ascarosides in *Caenorhabditis elegans*. To obtain a general picture of nematode sex pheromones, we purified the female sex pheromone of the sour-paste nematode, *Panagrellus redivivus*, and found that it is the ascaroside, ascr#1. The same chemical in *C. elegans* weakly induces diapause, suggesting that ascarosides might be a general class of nematode pheromones. Thus, the inventors performed a liquid chromatography mass spectrometric screen for ascarosides in 21 different nematode species, both free-living and parasitic. Many species produce species-specific but partially overlapping blends of ascarosides, indicating that ascarosides are highly conserved among nematodes. The inventors found that many nematodes also respond to ascarosides through attraction or repulsion, presenting possible new targets for the control of parasites.

Nematodes are the most abundant animals in the world. They have been found to inhabit sulfurous sediment, deep-sea trenches, human lymph nodes, pig intestines, plant roots, whale placenta, arctic ice, and many other ecosystems, making them one of the most successful groups of animals on earth. Nematodes are responsible for significant crop losses (~$100 billion annually) and most neglected tropical diseases (several hundred million affected individuals). Therefore it is no surprise that many nematode matefinding behaviors have been studied, in part towards the goal of developing methods for parasitic control. These studies collectively reveal that males from many nematode species are able to track females in environments as diverse as in plant roots, bacterial films, sand, agar, and mammalian intestines. There have also been many attempts to identify nematode pheromones, but identification has only been successful in two nematode species: the economically devastating soybean pathogen *Heterodera glycines* 26 and *Caenorhabditis elegans*. Since this discovery, chemical analogs of the *H. glycines* sex pheromone, vanillic acid has demonstrated potential to reduce parasitic load in affected crops by preventing males from finding their mates. Studies in the soil dwelling model organism *C. elegans* have shown that a family of small-molecule pheromones, called ascarosides, regulates gender specific attraction, repulsion, aggregation, olfactory plasticity, and entry into dauer (a stress-resistant life stage). These ascaroside studies were among the first to integrate modern advancements in analytical chemistry with the wealth of genetic, cellular, and developmental data available for *C. elegans*.

As further described herein, the inventors sought to purify pheromones from a diverse range of nematode species. Starting with the double-blind purification of the female sex pheromone in the sour-paste nematode *Panagrellus redivivus*, the inventors found that only one compound served as the male-attractant in the study, which the inventors then identified as ascr#1. Because ascr#1 is known for playing a small role in dauer induction in *C. elegans*, it is notable that the inventors found the same compound played a role in mate-finding in *P. redivivus*. Thus, the inventors believed that ascarosides are produced ubiquitously by nematodes.

For further investigation, the inventors collected worm excretions/secretions (E/S) from a wide range of both free-living and parasitic (plant, insect, and mammal) nematode species and screened for ascarosides in nematode byproducts. The inventors found that many nematodes indeed produce a wide range of ascarosides and that nematodes from several different genera are attracted to many of the same ascarosides, revealing that ascarosides are used by nematodes to communicate among species despite the fact that they occupy strikingly different ecologies. This universality presents a new paradigm in understanding of nematode communication, as this provides evidence of cross-species communication among members of this highly diverse metazoan phylum.

Example 2

The *Panagrellus redivivus* Female Sex Pheromone is an Ascaroside

The inventors developed several criteria for the nematode species that would ultimately be chosen for investigation for the activity-guided pheromone purification. The inventors wanted a nematode species that belonged to a different Glade than the species that have already had their pheromones identified (*H. glycines* and *C. elegans*). Given that activity-guided fractionation schemes have many involved steps and require many comparisons of nematode response to subtly different fractions, the inventors also wanted a nematode species that performs well on bioassays. For many of the species that the inventors had initially screened (*Koernia* sp., *Pristionchus pacificus*, *Pristionchus pauli*, *Acrobeles* sp., and *Zeldia* sp) individuals would move slowly, not at all, or in an inconsistent manner. The inventors chose the sour-paste nematode *Panagrellus redivivus* because both males and females move well and also because the preliminary experiments showed that both genders produce a sex pheromone that attracts the opposite gender. To score positive activity in this fractionation scheme, the inventors developed a semi-automated attraction assay to look for attraction to a given cue (FIG. 1). The inventors combined this scoring method with a previously described fractionation scheme (FIG. 2a). Specifically, nematode-conditioned media was fractionated based on hydrophobicity (FIG. 2b) and charge (FIG. 2c); then two positive fractions were further separated by HPLC (FIG. 2d). Through this process, the inventors discovered a single male-attracting component that was being produced by females, but not males. They used nuclear magnetic resonance (NMR) spectroscopy and liquid chromatography mass spectrometry (LCMS) to identify this compound as (−) 6-(3,5-dihydroxy-6-methyltetrahydropyran-2-yloxy) heptanoic acid (aka ascr#1, C736 or daumone28) (FIG. 2a).

To confirm activity of the identified ascaroside, the inventors tested synthetic samples of ascr#1 to confirm activity and found that *P. redivivus* males were strongly attracted to synthetic ascr#1 over a wide range of concentrations, with no apparent attenuation of high concentrations (FIG. 2e). In this regard, the response of *P. redivivus* males to ascr#1 differs from that of *C. elegans* males to two different *C. elegans* hermaphroditic sex pheromones, ascr#2 and ascr#3, as well as unfractionationated hermaphroditie exudates, both of which show a biphasic response with reduced attraction at high concentrations of ascarosides.

Next the inventors tested to see if ascr#1 is a gender-specific pheromone and found that female *P. redivivus* were not attracted to ascr#1 at any of the tested concentrations (FIG. 2e), allowing the conclusion that ascr#1 is indeed the male-specific attractant. *P. redivivus* females were not significantly repelled by ascr#1, as measured by the semi-automated scoring method; however, detailed inspection of the videos recorded from the assays revealed that females showed some repulsive behavior: they tended to stall upon entering the region holding the ascr#1 sample spot, followed by a change in direction and abrupt exit of the region. Because there is a delay before females exit from the ascr#1 sample spot, time spent in the ascr#1 sample spot was comparable to the time spent in the control region, preventing detection of repulsion by our automated assay. The inventors thus used a separate method for scoring repulsion that focused on behavioral response rather than time spent in each region. Defining repulsion as the immediate exit of the conditioned region before entering a full worm's length, the inventors found that females were significantly repelled by high concentrations of ascr#1. It can be concluded that the *P. redivivus* female sex pheromone is ascr#1, which strongly attracts males but repels females at high concentrations.

Therefore, *P. redivivus* and *C. elegans* use structurally related small molecules as chemical signals. This result was unexpected given that *P. redivivus* and *C. elegans* belong to two different clades of nematode genera. Because ascr#1 has already been characterized in *C. elegans* for its limited role in the induction of a diapausal life stage, the findings demonstrate that the same ascaroside can serve different functions between different species and between different genders.

Example 3

Ascarosides are Broadly Present in Many Nematodes

Based on the conclusion that the *C. elegans* pheromone, ascr#1, also serves as a pheromone in *P. redivivus*, the inventors believed that ascarosides may represent a general class of nematode signaling molecules and initiated a mass-spectrometry-based screen for ascarosides in a larger selection of nematode species. The inventors included nematodes with different types of life histories, including both parasites (plant, insect and mammal) and free-living nematodes. The screen further included species from ancestral Clade 2 and the more recently evolved Clade 12.

Sample selection was opportunistic in that the inventors used metabolite samples obtained from mixed populations, such that there could be gathered a wide sampling of ascarosides across all larval stages. For many parasitic nematodes, infective juveniles were separated from adults to look for differences between chemical cues produced during the host-seeking life stage and mate-seeking life stage. For metabolite collection, nematodes were generally incubated with appropriate buffer for a few hours and then filtered out. The resulting metabolite extracts were analyzed via HPLC-ESI-MS using a protocol specifically optimized for the detection of ascarosides in complex metabolome samples. These analyses revealed the presence of ascarosides in most of the nematode samples. Comparison with mass spectroscopic data and retention times of a library of 150 ascarosides known from *C. elegans* led to the identification of a total of 19 different ascarosides in the 21 species analyzed.

Ascaroside profiles generally varied between species; however, in some cases even entirely unrelated species produced surprisingly similar ascaroside mixtures. For example, a highly diverse range of nematodes produced the saturated ascaroside ascr#10, including the rat parasitic nematode *Nippostrongylus brasiliensis*, the entomopathogenic insect nematodes *Heterorhabditis bacteriophora, Steinernema carpocapsae, Steinernema glaseri*, and *Steinernema riobrave*, the soil nematode *Caenorhabditis elegans*, and the necromenic insect parasites *Pristionchus pacificus* and *Koernia* sp.

It should be noted that although all of the identified ascarosides have previously been found in *C. elegans* metabolite extracts, most of these are not produced by *C. elegans* wild type and were identified from metabolite extracts of specific *C. elegans* mutants. This observation suggests that whereas nematodes have the capability to produce a great diversity of ascaroside derivatives, the abundance and proportions of the various ascaroside blends are species specific.

Several other species including *H. bacteriophora* and *P. strongyloides* predominantly contained longer chained ascarosides with 11-15 numbered carbon side-chains. In some cases, ascarosides with saturated 5-, 7-, 9-, and 11-numbered carbon side chains, e.g. *Caenorhabditis elegans* and *Rhabditis* sp. extracts, were accompanied by additional lateraleluting isomeric derivatives whose mass spectra suggests that they represent derivatives carrying the ascarylose unit on the ultimate carbon of the side chain, instead of the usual penultimate position. The structures of these omega-oxygenated ascarosides ("oscr") was confirmed by synthesis of two representative components featuring five- and nine-carbon side chains (compounds oscr#9 and oscr#10).

Some of the known ascarosides were not found in some nematode species, namely *Pratylenchus* species, *Heterodera. schactii, Ascaris suum*, and *Romanomermis* species; however, it is possible that these species produce ascarosides in amounts smaller than detection limit, or that their biosynthesis occurs only under environmental conditions different from those in the current study. For example, the parasitic species (*Pratylenchus* sp. and *Heterodera schactii*) have a plant-adjacent lifestyle and the *Romanomermis* species have a mosquito-infective and moss-dwelling lifestyle that might require collection conditions that mimic their environments more closely. It is also possible that some of the species analyzed produce ascarosides with structural modifications that prevented their identification in our mass spectrometric screen.

Finally, the inventors applied the MS screen to *Panagrellus redivivus*, given that the results for ascr#1 described herein were found using traditional activity-guided fractionation. Large quantities of two ascarosides, ascr#1 and ascr#10 in *P. redivivus* females were found, which were absent in metabolite samples obtained from males. This finding supports the discovery that ascr#1 is indeed a *P. redivivus* female sex pheromone. Following the additional identification of ascr#10 in female *P. redivivus* samples, the inventors tested both males and females for attraction by ascr#10. Females do not respond to ascr#10 at any of the concentrations tested; whereas males show some attraction at the very high, nonphysiological concentration of 1 mM. Because such high concentrations were not tested during the activity-guided isolation of the female pheromone, ascr#10 was not discovered along with ascr#1.

Example 4

Different Species of Nematodes are Attracted to Ascarosides

To investigate the biological function of the ascarosides identified in the MS screen, the inventors used a bioassay (FIG. 1) to measure attraction of different nematode species to a wide range of ascaroside concentrations (1 nM, 1 µM, and 1 mM). For these bioassays, nematode species had to fulfill several requirements, such as sufficient movement on bacterial lawns, low tendency to aggregate, easy to grow, and generally reproducible locomotive behavior. This study was limited to a survey of males from different species, because males tended to move much more evenly across our bioassay lawn than females and hermaphrodites (with the exception of *P. redivivus* females, which move well and were therefore in this study.)

Figure 4:
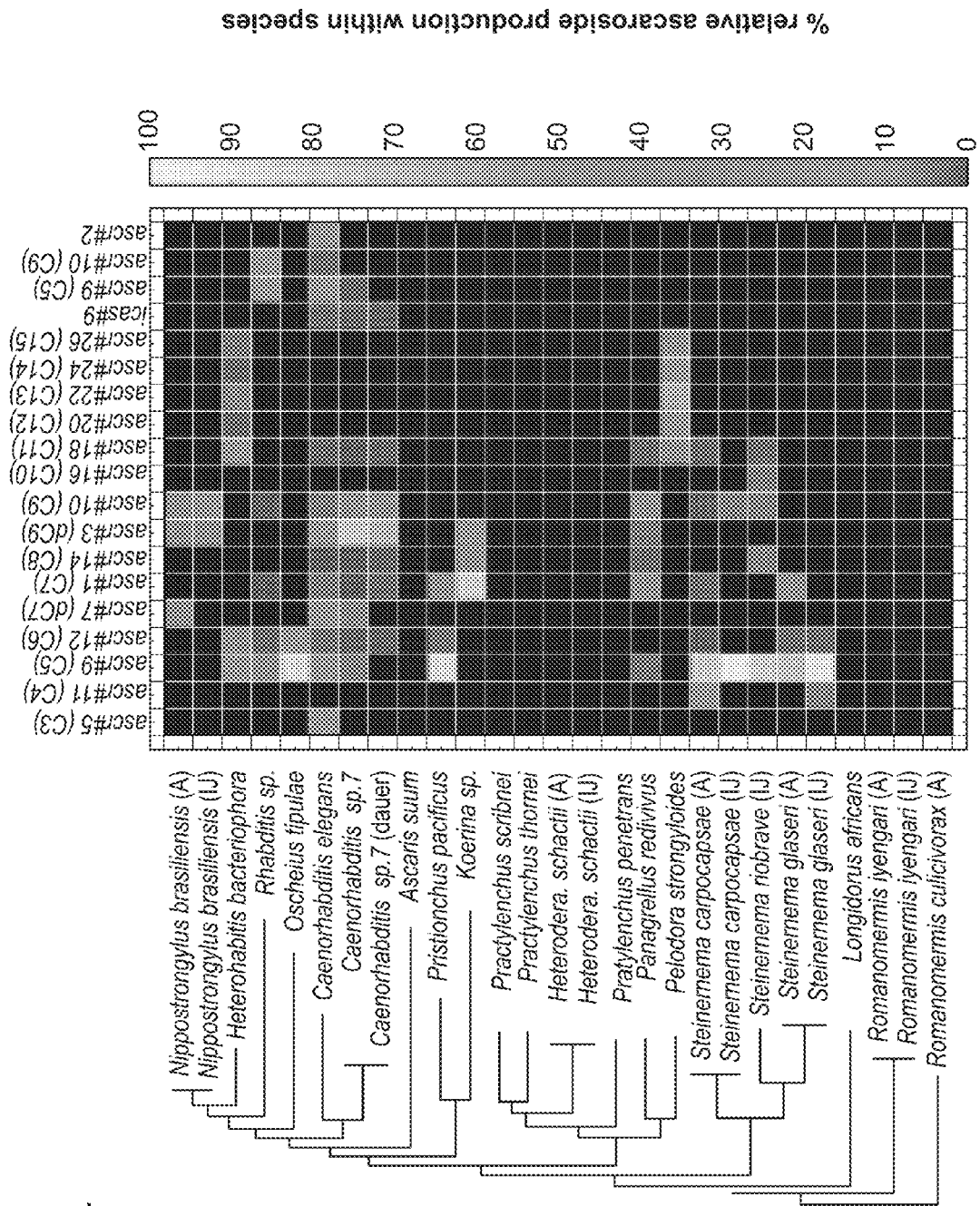
FIG. 4 depicts, in accordance with an embodiment herein, that ascarosides are produced by a wide range of nematode species. Results from the HPLC-MS analysis of worm media samples obtained from incubating worms for 6 h at 1 worm/μL. Parasitic species indicated as infective juveniles (IJ) and adults (designated as "A") were collected separately; all other samples were obtained from mixed stage cultures. Many nematodes produce species-specific, but partially overlapping blends of ascarosides. Colors in this heatmap represent different relative abundance of ascarosides in the analyzed species.
Figure 5:
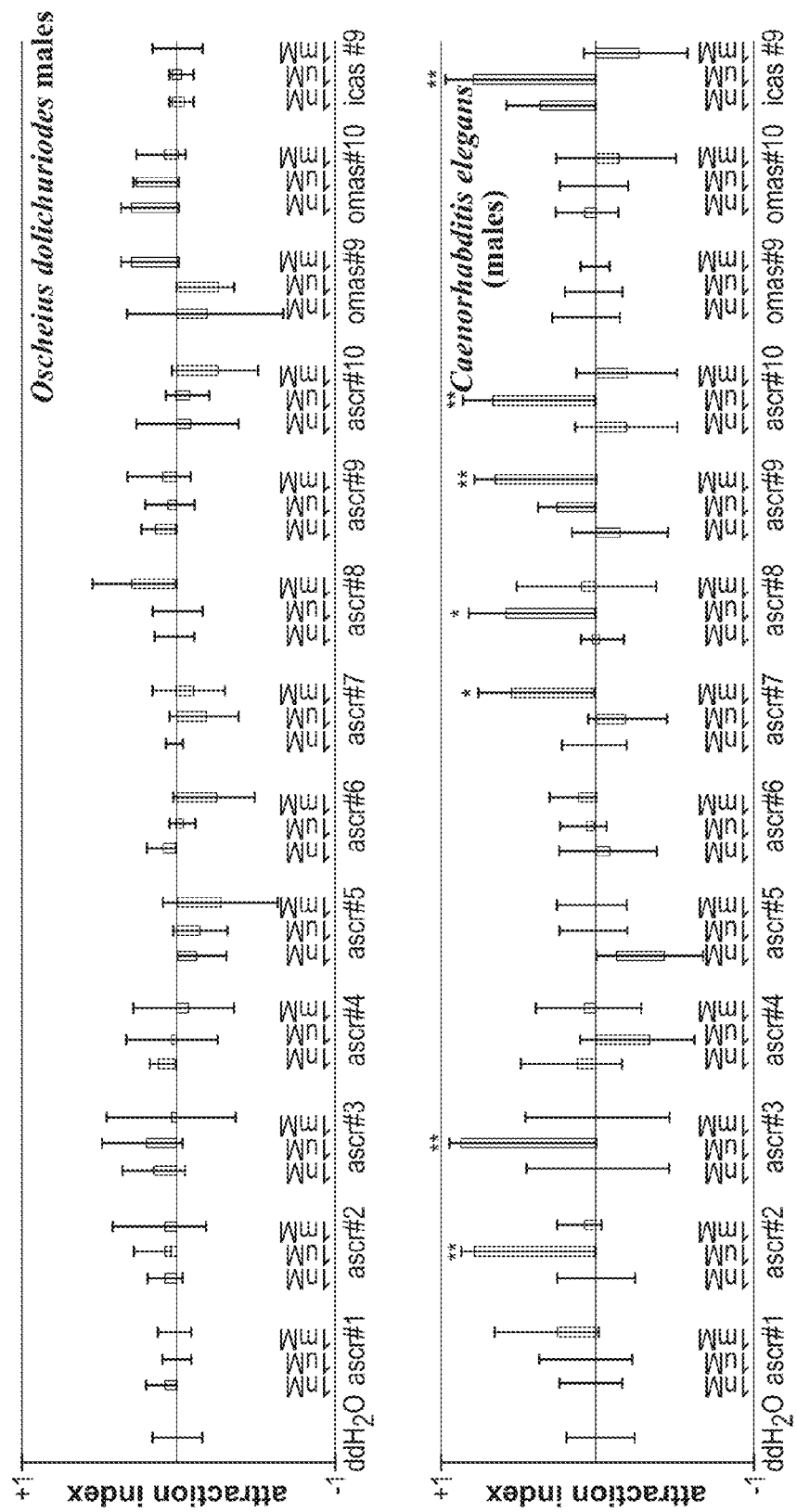
FIG. 5 depicts, in accordance with an embodiment herein, that ascarosides mediate behavior of nematode species from diverse generas. Species that were amenable to test in the attraction assay (sufficient movement, unbiased direction, reproducible controls) were scored for attraction or repulsion toward three concentrations (1 mM, 104, and 1 nM: from left to right) of 13 different ascarosides. Pvalues were determined using the Student's t-test with a P<0.05. The score "0" represents any findings where P>0.05.
Figure 5:
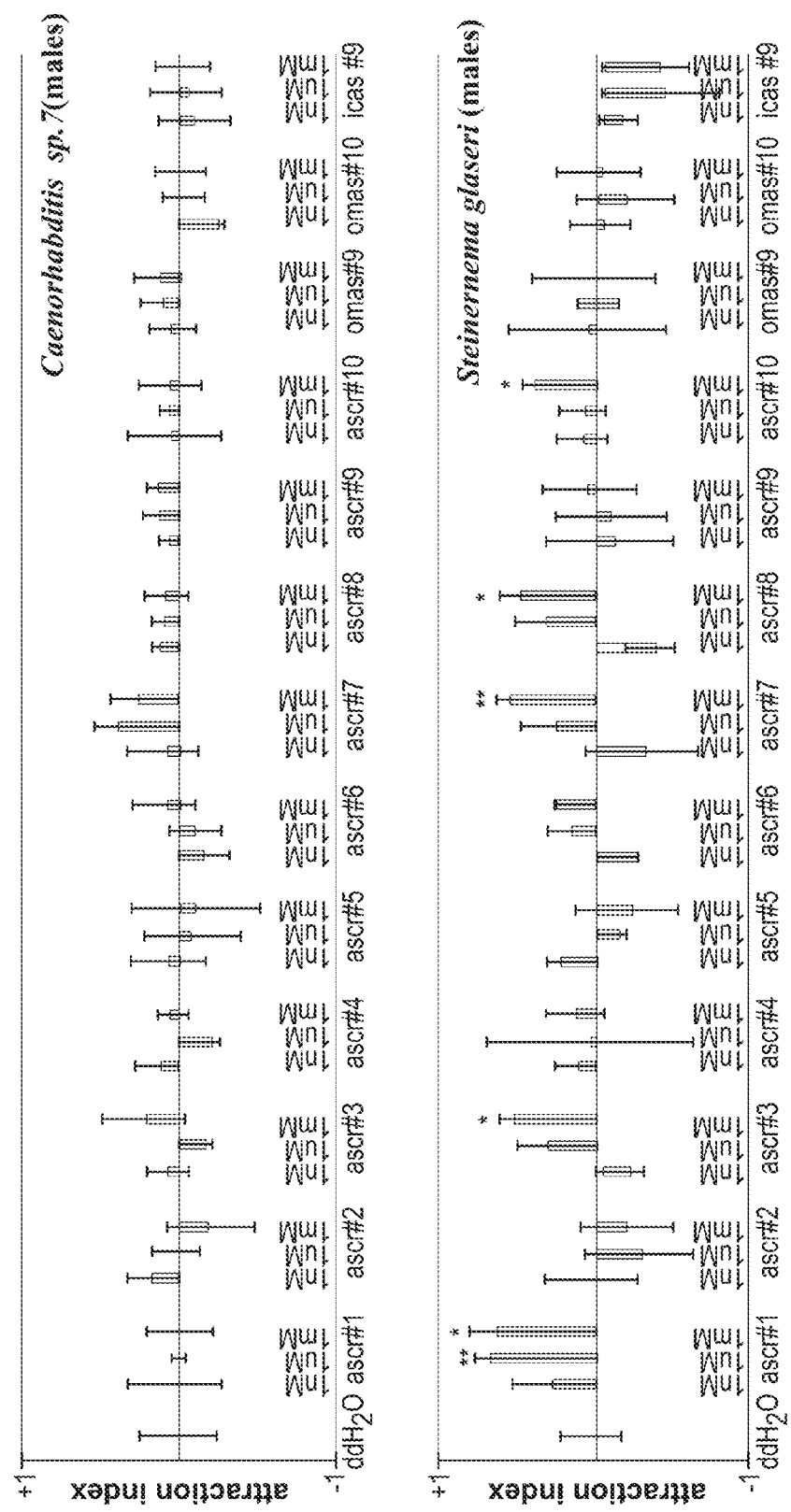
Figure 5:
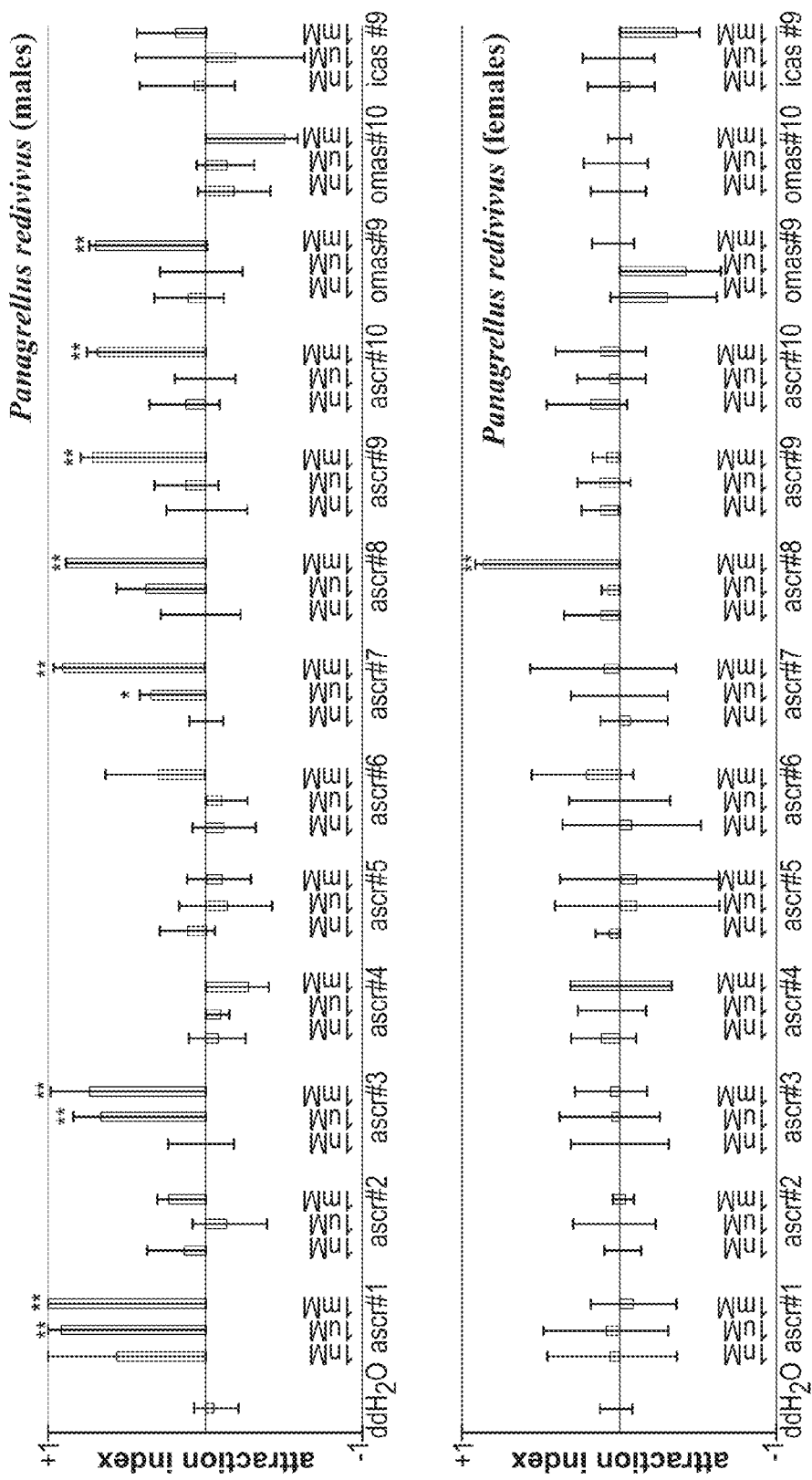
Figure 6:
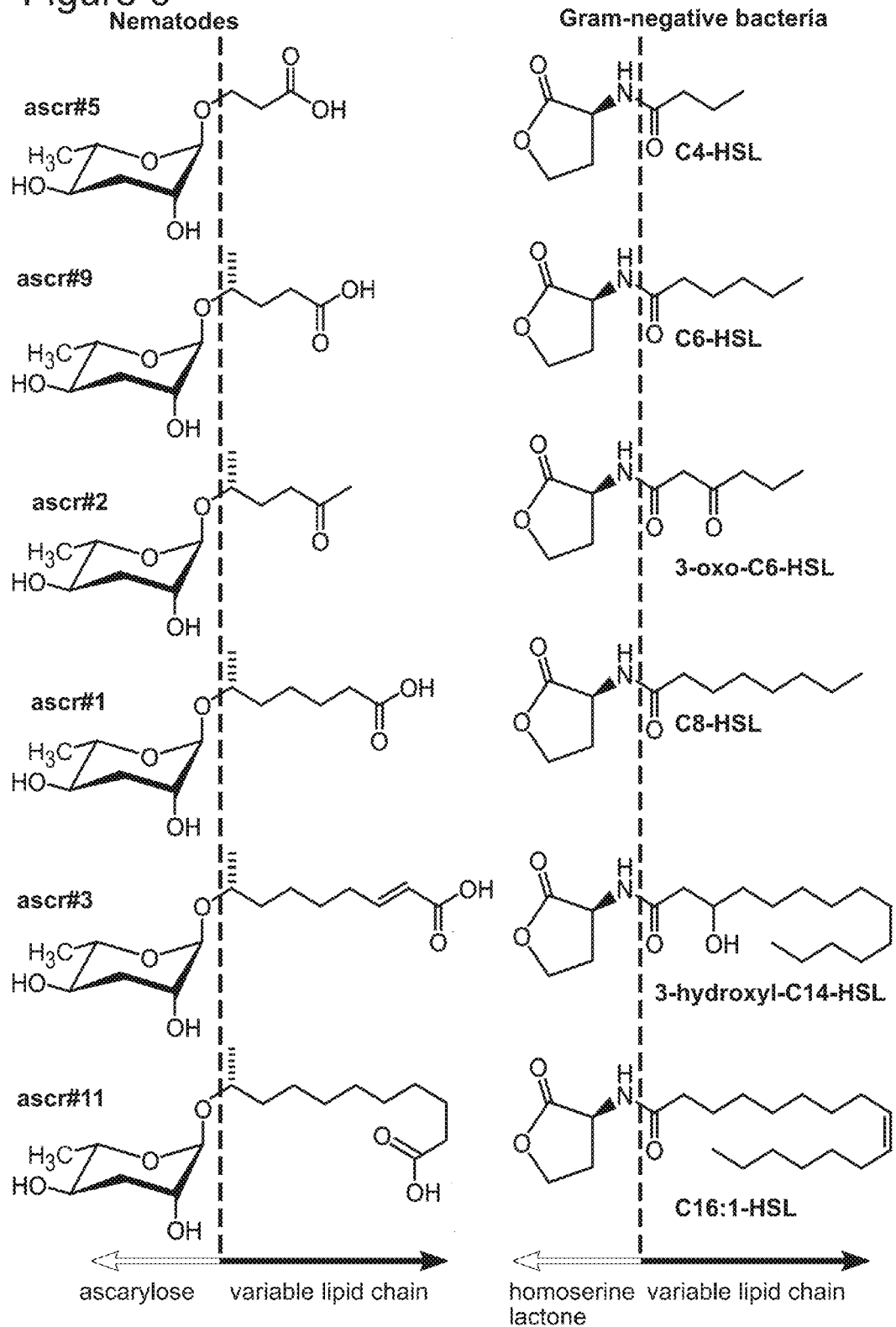
FIG. 6 depicts, in accordance with an embodiment herein, similar assembly of signaling molecules in nematodes and bacteria. N-acyl homoserine lactones (AHLs) play important roles in bacterial quorum sensing and are produced and sensed by many Gramnegative as well as some Grampositive bacteria. All AHLs are based on homoserine lactone and feature species-specific variations in the N-acyl chain. Ascarosides are assembled in a very similar fashion, based on the dideoxysugar ascarylose as invariable scaffold to which a variable lipid chain is attached.
Figure 8:
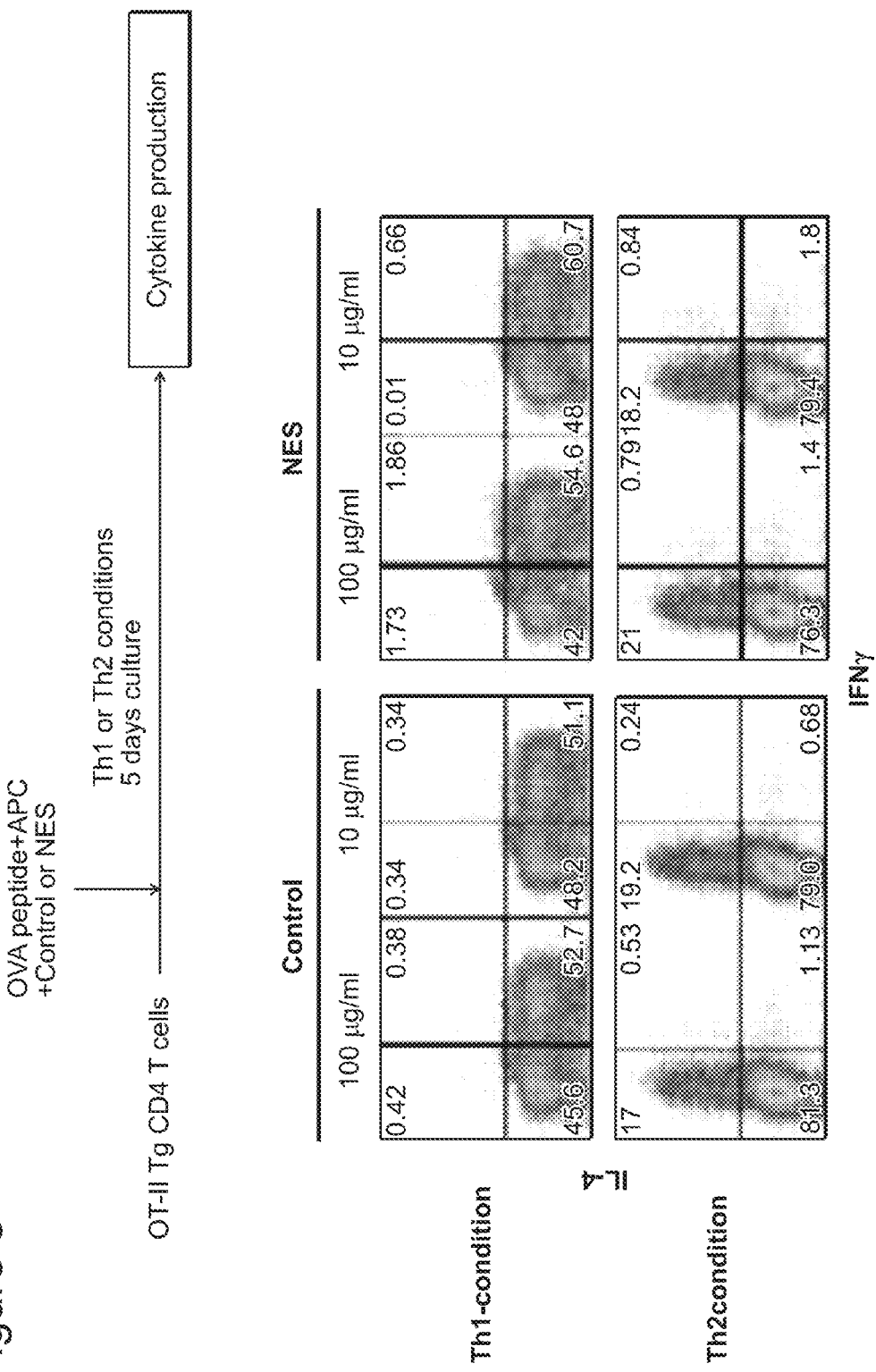
FIG. 8 depicts, in accordance with an embodiment herein, in vitro differentiation of Th1/Th2 cells. The effect of NES on the differentiation of Th1/Th2 cells is examined. There does not seem to be a direct effect of NES on the differentiation of Th1/Th2 in terms of IL-4/IFNg production.
Figure 9:
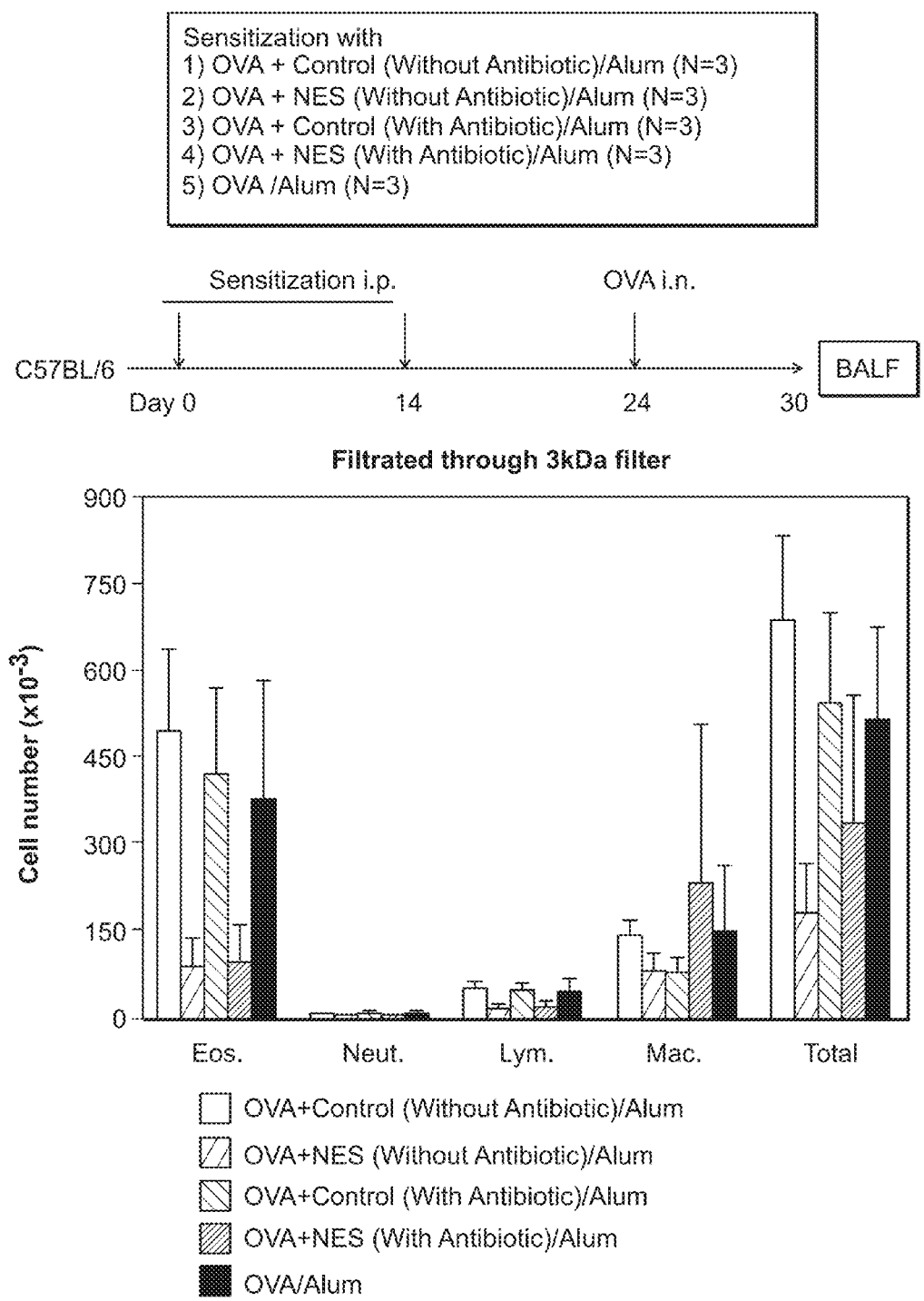
FIG. 9 depicts, in accordance with an embodiment herein, in vitro differentiation of Th1/Th2 cells. The effect of the antibiotic is examined, where NES appears to be effective with antibiotics and does not negatively disrupt the mouse gut.
Figure 10:
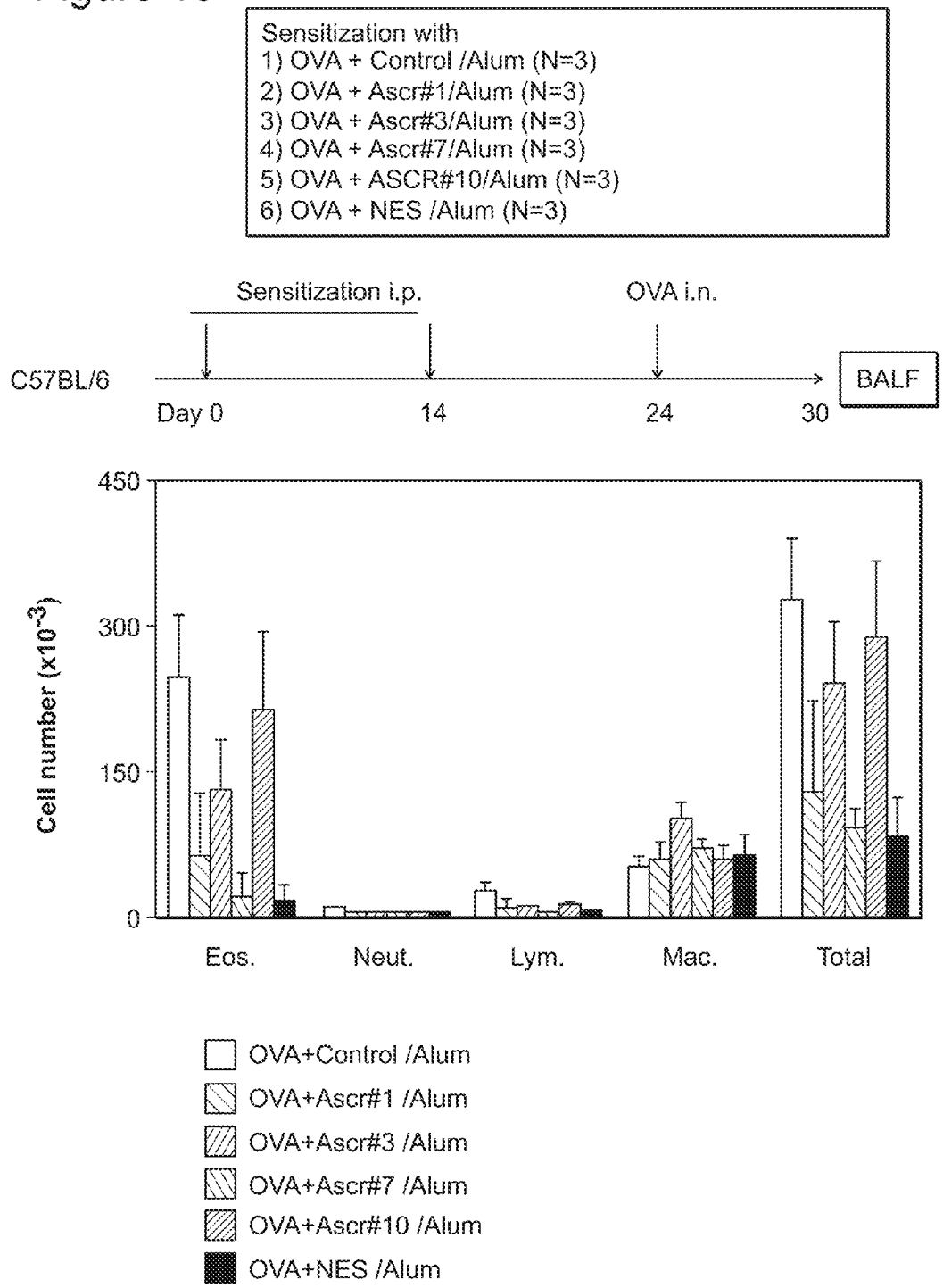
FIG. 10 depicts, in accordance with an embodiment herein, synthesized ascrs demonstrates reduction in eosinophils. The effects of ascarosides are examined for an allergic airway inflammation. It appears that especially Ascr#7 has an inhibitory effect for allergic airway inflammation. The inventors demonstrated that ascr#1, 3, 7, and 10 was produced in *Nippostrongylus brasiliensis*, and then tested synthesized compounds individually. The reduction of eosinophils are markedly reduced when given very small amounts of ascr#7 (purple), comparable to the effect of total hookworm supernatant (black bar). Ascr#1 and ascr#3 show some effect as well.

The inventors found that males from many of the nematode species tested were attracted to the same ascarosides, particularly ascr#1, ascr#3, ascr#7, ascr#8, ascr#9, and ascr#10 (FIG. 4). Several nematodes respond to different concentrations of ascarosides, for example *P. redivivus* males are attracted to 1 mM and 1 µM of ascr#7, whereas *C. elegans* males only respond to 1 mM. This may help to create species-specific chemical signatures that are made up of different blends of ascarosides.

Example 5

Conclusions

Ascarosides could represent a universal nematode language, given their widespread production and recognition by free-living and parasitic nematodes. These findings are evocative of inter-species quorum sensing molecules, Nacyl homoserine lactones (AHLs), which are both produced and sensed by many Gramnegative bacteria. AHLs are composed of the same homoserine lactone but have species-specific variations in the N-acyl chain40. Ascarosides are organized in a very similar fashion; they are composed of the same ascarylose sugar ring but have variations in the attached fatty acid tail. The inventors believe this similar-but-different organization of pheromones helps species to facilitate both intra-specific and inter-specific communication. This design may also be useful to modify signals with limited cost, allowing nematodes to produce a variety of cues as necessary. A possible mechanism of modifying preexisting ascarosides might help to produce communicative signals quickly during times when swift response is necessary.

For the same reason that there has been disagreement regarding the uncertainty of shared motives for quorum-sensing bacteria, there may not be a unanimous motive for ascaroside production or recognition. It is clear that ascarosides are used for different reasons both between and within species, given that ascr#1 plays a small role in *C. elegans* dauer formation and since ascr#1 attracts *P. redivivus* males and repels *P. redivivus* females. Intraspecific discretion might be achieved by the production of a unique blend of ascarosides and/or the existence of different response thresholds. The findings support this possibility, given that nematodes produce different relative quantities of ascarosides and sometimes respond to different concentrations of the same ascaroside. Because recombination is a theme often used in nature to achieve variation, it is not unlikely that nematodes secrete combinations from the same repertoire of ascarosides to present a specific chemical signature to their surrounding environment. Once they are secreted into the environment, ascarosides may potentially be used by nematodes for any number of reasons, such as predation, food sharing, coordinated defense, cohabitation, diapause, mate-finding, aggregation, etc. Ascarosides mediate stress-resistance, mate finding, and clustering behavior. These survival strategies might be useful for the selective inhibition of a parasite's induction into its infectious stage, ability to find mates, or their ability to mount a coordinated defense against predators. Alteration of the concentration and/or combination of ascarosides may also be useful to promote nematode survival, as there are also many beneficial uses for nematodes. For example, nematodes from the genus *Heterorhabditis* are being used as a biological control agent for the eradication of black vine weevils, citrus fruit weevils, fleas, wood boring leps, mushroom flies and many other agricultural pests. Lastly, the discovery of a common language between nematodes provides new insight into mechanisms of animal communication, given that the discovery of ascarosides as a shared nematode language represents a step toward understanding small molecule signaling in this most abundant group of metazoans.

Example 6

Methods—Attraction Assay

OP50 E. coli is grown on a standard 5 cm agar plate (made with standard Nematode Growth Medium). The bacterial lawn is 16 mm in diameter and is grown overnight at 20 C before being used in trials. Two 4-mm spots (0.6 L) were placed on opposite sides of the bacterial lawn (using a transparent template to guide spot placement) and several minutes elapsed for the liquid to settle in before placing nematodes down on the assay. Recording began immediately upon worm placement. 0.6 L of the control was placed on one side of the lawn and 0.6 L of the experimental cue was placed on the other side of the lawn, changing the location of the cue throughout trials, between left/right and top/bottom to avoid bias. Nematodes were isolated by gender at the L4 stage the day before being used in trials as developed adults. Five worms were each placed at two points equidistant from the foci of the scoring region (ten total). Trials were recorded for 20 minutes and frames were collected for analysis at 1 frame per second. Results were averaged from at least three different trials. For every nematode species in this study, the inventors tested different total number of worms (using water in both scoring regions) to determine the minimum number of worms necessary for consistent unbiased results over a 20-minute trial. The total number of worms used in the multiple species assays depending on that species' optimal parameters. 10 worms were for P. redivivus males and females, 20 worms were used for C. elegans males, O. dolichuridae males, and C. sp7 males and 14 worms were used for S. glaseri males.

Example 7

Methods—Automated Software

A video camera attached to the microscope produces a digital video stream, which is then analyzed. The ratio of time the average worm spends in each region of interest is calculated for every trial. For ease of implementation, it was assumed that all worms in a single experiment are roughly the same size. Thus, worm pixels were counted instead of whole worms, allowing the inventors to take into account fractions of a worm in the region of interest. It also eliminated the need for a shape-based worm identification algorithm, and allowed each frame to be analyzed independently. The inventors applied a band-pass filter to each frame to eliminate the effect of uneven lighting and also accentuate the worms against the background. The worm was then identified after thresholding the filtered image. Throughout each experiment, the inventors know the locations and sizes of the regions of interest. Through the filtering described above, the inventors know which pixels are occupied by worms and which ones are not. They are then able to calculate the ratio of worm-pixels to all pixels inside the region of interest to produce the worm-occupancy ratio. This is done for every frame, giving a plot output of worm-occupancy ratio vs. time for each region.

Example 8

Dauer Assay

The inventors adapted the dauer assay from Butcher et al. (2008) and used liquid cultures instead of agar plates. Nematode embryos were synchronized by bleaching twice (3 hours apart) and collected in S Complete for liquid culture. They were grown in 4 mg/mL HB101 E. coli at a density of 6 worms per L, along with no ascarosides or 220 nM of the ascaroside. They were incubated at 20 C for 4 days, after which they were scored for % dauer formation using observation of anatomical changes and 2% SDS survival tests. Several hundred worms were scored for each trial, with an average of at least three trials.

Example 9

Activity-Guided Fractionation

Activity-Guided Fractionation and NMR and HPLC-MS analysis of ascr#1 from P. redivivus was similar to protocols developed for C. elegans mating pheromones.

The various methods and techniques described above provide a number of ways to carry out the invention. Of course, it is to be understood that not necessarily all objectives or advantages described may be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as may be taught or suggested herein. A variety of advantageous and disadvantageous alternatives are mentioned herein. It is to be understood that some preferred embodiments specifically include one, another, or several advantageous features, while others specifically exclude one, another, or several disadvantageous features, while still others specifically mitigate a present disadvantageous feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be mixed and matched by one of ordinary skill in this art to perform methods in accordance with principles described herein. Among the various elements, features, and steps some will be specifically included and others specifically excluded in diverse embodiments.

Although the invention has been disclosed in the context of certain embodiments and examples, it will be understood by those skilled in the art that the embodiments of the invention extend beyond the specifically disclosed embodiments to other alternative embodiments and/or uses and modifications and equivalents thereof.

Many variations and alternative elements have been disclosed in embodiments of the present invention. Still further variations and alternate elements will be apparent to one of skill in the art. Among these variations, without limitation, are the selection of constituent modules for the inventive compositions, and the diseases and other clinical conditions that may be diagnosed, prognosed or treated therewith. Various embodiments of the invention can specifically include or exclude any of these variations or elements.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

In some embodiments, the terms "a" and "an" and "the" and similar references used in the context of describing a particular embodiment of the invention (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventors for carrying out the invention. Variations on those preferred embodiments will become apparent to those of ordinary skill in the art upon reading the foregoing description. It is contemplated that skilled artisans can employ such variations as appropriate, and the invention can be practiced otherwise than specifically described herein. Accordingly, many embodiments of this invention include all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above cited references and printed publications are herein individually incorporated by reference in their entirety.

In closing, it is to be understood that the embodiments of the invention disclosed herein are illustrative of the principles of the present invention. Other modifications that can be employed can be within the scope of the invention. Thus, by way of example, but not of limitation, alternative configurations of the present invention can be utilized in accordance with the teachings herein. Accordingly, embodiments of the present invention are not limited to that precisely as shown and described.

The invention claimed is:

1. A method of alleviating or treating an inflammatory disorder in a human subject, comprising:
   administering to the subject a composition comprising isolated ascr#7

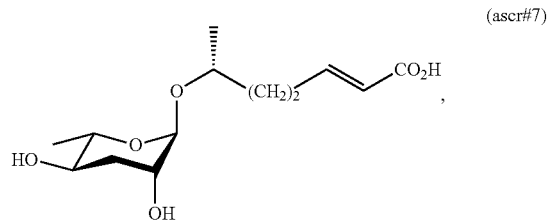

(ascr#7)

or a salt thereof; and
   wherein the inflammatory disorder is asthma, inflammatory bowel disease, or type one diabetes.

2. The method of claim 1, wherein the method reduces mucus production in the subject.

3. The method of claim 1, wherein the naturally occurring ascaroside is produced from a *Nippostrongylus brasiliensis*.

4. The method of claim 1, wherein the inflammatory disorder is asthma.

5. The method of claim 1, wherein the inflammatory disorder is inflammatory bowel disease.

6. The method of claim 1, wherein the inflammatory disorder is type one diabetes.

* * * * *